United States Patent
Wolfe et al.

(10) Patent No.: US 6,323,366 B1
(45) Date of Patent: Nov. 27, 2001

(54) ARYLAMINE SYNTHESIS

(75) Inventors: John P. Wolfe, Brighton; Jens Ahman, Cambridge; Joseph P. Sadighi, Boston; Robert A. Singer, Belmont; Stephen L. Buchwald, Newton, all of MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 09/122,324

(22) Filed: Jul. 24, 1998

Related U.S. Application Data

(60) Provisional application No. 60/054,092, filed on Jul. 29, 1997.

(51) Int. Cl.$^7$ .................................................. C07C 249/02
(52) U.S. Cl. .......................... 564/269; 546/181; 546/311; 549/451; 560/19; 560/35
(58) Field of Search .................................... 546/181, 311; 549/451; 560/19, 35; 564/269

(56) References Cited

U.S. PATENT DOCUMENTS

| | | | |
|---|---|---|---|
| 3,657,430 | * 4/1972 | Shen et al. | 424/230 |
| 4,096,185 | 6/1978 | Seiwell et al. | 260/581 |
| 4,204,997 | 5/1980 | Hobbs et al. | 260/326.8 |
| 5,576,460 | 11/1996 | Buchwald et al. | 564/386 |
| 5,739,396 | 4/1998 | Trost et al. | 564/15 |

FOREIGN PATENT DOCUMENTS

| | | |
|---|---|---|
| 2 474 491 | 7/1981 | (FR) . |
| 1047925 | 11/1966 | (GB) . |
| 09239275 | 9/1997 | (JP) . |
| WO 96/09306 | 3/1996 | (WO) . |
| WO 97/05104 | 2/1997 | (WO) . |
| WO 97/13763 | 4/1997 | (WO) . |
| WO 98/15515 | 4/1998 | (WO) . |

OTHER PUBLICATIONS

Driver, et al., "A Second–Generation Catalyst for Aryl Halide Amination: Mixed Secondary Amines from Aryl Halides and Primary Amines Catalyzed by (DPPF)PdCl2", *J. Am. Chem. Soc.*, 118, pp. 7217–7218, 1996.

Hamann, et al., "Systematic Variation of Bidentate Ligands Used in Aryl Halide Amination. Unexpected Effects of Steric, Electronic, and Geometric Perturbations", *J. Am. Chem. Soc.*, 120, pp. 3694–3703, 1996.

Hartwig, et al., "Influences on the Relative Rates for C–N Bond–Forming Reductive Elimination and B–Hydrogen Elimination of Amides. A Case Study on the Origins of Competing Reduction in the Palladium–Catalyzed Amination of Aryl Halides", *J. Am. Chem. Soc.*, 118, pp. 3626–3633, 1996.

Hartwig, "Palladium–Catalyzed Amination of Aryl Halides: Mechanism and Rational Catalyst Design", *Synlett*.

Louie, et al., "Catalysis with Platinum–Group Alkylamido Complexes. The Active Palladium Amide in Catalytic Aryl Halide Aminations as Deduced from Kinetic Data and Independent Generation", *Organometallics*, 15, pp. 2794–2805, 1996.

Louie, et al., "Palladium–Catalyzed Synthesis of Arylamines from Aryl Halides. Mechanistic Studies Lead to Coupling in the Absence of Tin Reagents", *Tetrahedron Letters*, vol. 36, No. 21, pp. 3609–3612, 1995.

Mann, et al., "Palladium–Catalyzed C–N(sp2) Bond Formation: N–Arylation of Aromatic and Unsaturated Nitrogen and the Reductive Elimination Chemistry of Palladium Azolyl and Methyleneamido Complexes", *J. Am. Chem. Soc.*, 120, pp. 827–828, 1998.

Molina, et al., "Synthesis and Structure of P,N–Heterodifunctional Ferrocene Ligands and their Transition Metal Complexes for Palladium–Catalyzed Aryl Amination Reaction", *Tetrahedron Letters*, vol. 38, No. 43, pp. 7613–7616, 1997.

Paul, et al., "Palladium–Catalyzed Formation of CarbonNitrogen Bonds. Reaction Intermediates and Catalyst Improvements in the Hetero Cross–Coupling of Aryl Halides and Tin Amides", *J. Am. Chem. Soc.*, 116, pp. 5969–5970 1994.

Paul, et al., "Structural Characterization and Simple Synthesis of {Pd[P(o–Tol)3]2}, Dimeric Palladium (II) Complexes Obtained by Oxidative Addition of Aryl Bromides, and Corresponding Monometallic Amine Complexes", *Organometallics*, 14, pp. 3030–3039.

Perry, et al., "Synthesis of 2–Arylbenzoxazoles via the Palladium–Catalyzed Carbonylation and Condensation of Aromatic Halides and o–Aminophenols",*J. Org. Chem.*, 57, pp. 2883–2887, 1992.

Trost, et al., "An Approach to Primary Allylic Amines via Transition–Metal–Catalyzed Reactions. Total Synthesis of (+/−)–Gabaculine", *The Journal of Organic Chemistry*, vol. 44, No. 20, Sep. 28, 1979.

(List continued on next page.)

*Primary Examiner*—Peter O'Sullivan
(74) *Attorney, Agent, or Firm*—Dana M. Gordon; Foley, Hoag & Eliot LLP

(57) ABSTRACT

The present invention provides a method for the preparation of a wide range of primary arylamines. The arylamines are prepared in two efficient, straightforward transformations: 1) an activated aryl group and an imine group are combined, in the presence of a transition metal catalyst, under conditions wherein the transition metal catalyst catalyzes the formation of a carbon-nitrogen bond between the activated carbon of the arene and the imine nitrogen; and 2) the resulting N-aryl imine is transformed, via any of a number of standard protocols, to the primary arylamine. The method of the invention may also be exploited in the preparation of vinylamines.

88 Claims, No Drawings

OTHER PUBLICATIONS

Wolfe, et al., "An Ammonia Equivalent for the Palladium-Catalyzed Amination of Aryl Halides and Triflates", *Tetrahedron Letters*, vol. 38, No. 36, pp. 6367–6370, 1997.

Wolfe, et al., "Palladium–Catalyzed Amination of Aryl Iodides", *J. Org. Chem.*, 61, pp. 1133–1135, 1996.

Wolfe, et al., "Palladium–Catalyzed Amination of Aryl Triflates", *J. Org. Chem.*, 62, pp. 1264–1267, 1997.

Yamamoto, et al., "Palladium–Catalyzed Synthesis of Triarylamines from Aryl Halides and Diarylamines", *Tetrahedron Letters*, 39, pp. 2367–2370, 1998.

* cited by examiner

ARYLAMINE SYNTHESIS

RELATED APPLICATION

This application claims priority to U.S. Ser. No. 60/054,092, filed Jul. 29, 1997.

GOVERNMENT FUNDING

This invention was supported in part with funds provided by the National Science Foundation and the Office of Naval Research. The government has certain rights in the invention.

BACKGROUND OF THE INVENTION

The arylamine moiety is a structural component in a variety of synthetic and naturally occurring biologically active compounds. For instance, arylamines are useful in a variety of applications such as in the preparation of dyes, herbicides, insecticides, pharmaceuticals, plant growth agents and antiknock agents for gasoline engines.

To further illustrate, primary anilines find a variety of utilities. p-Aminodiphenylamine is an important intermediate in the synthesis of antioxidants and antiozonants for rubber. Phenylenediamines, particularly $C_5$–$C_{10}$ alkyl-substituted derivatives thereof, are also useful in stabilizing rubbers. p-Aminophenols are useful as chemical intermediates. For example, p-hydroxyaniline is employed in the manufacture of analgesics and antipyretics. Other substituted phenylamines, such as chloroanilines, are useful in the manufacture of dyes, medicinals, and resins.

Notwithstanding recent progress in the development of methods for the transition metal-catalyzed formation of carbon-heteroatom bonds, construction of the carbon-nitrogen bond of arylamines and vinylamines remains a synthetic challenge in certain cases. See, inter alia: U.S. Pat. No. 5,576,460; *Angew. Chem., Int. Ed. Engl.* 1995, 34, 1348; *J Am. Chem. Soc.* 1996, 118, 7215; *Tetrahedron Lett.* 1996, 52, 7525; and references cited therein. In particular, a number of synthetic methods for the construction of such an aryl-nitrogen bond suffer from severe reaction conditions and/or are only applicable to activated substrates. Typical routes to aromatic amines include nucleophilic aromatic substitution of electron-poor aryl precursors. See, Hattori et al. (1994) *Synthesis* 1994:199; and Bunnett, J. F. (1978) *Acc. Chem. Res* 1978 11:413. Synthesis of arylamines via copper-mediated Ullmann-like condensation reactions has also been reported. See, for example, Paine (1987) *J. Am. Chem. Soc.* 109:1496. The copper-catalyzed preparation of aryl amines, such as anilines and substituted anilines, by amination of an aryl halide is also described in U.S. Pat. No. 4,096,185, which discloses the preparation of p-aminobenzotrifluoride by reaction of p-chlorobenzotrifluoride with ammonia in the presence of a copper halide catalyst.

Primary anilines are often prepared by nitration of an arene, followed by reduction of the resulting nitroarene compound. The success of this approach hinges on three basic issues: 1) the availability of the arene starting material; 2) the ability to prepare the desired nitro compound from the arene; and 3) the ability to reduce selectively the nitro group to the corresponding primary aniline. This approach to anilines has certain inherent limitations. In some instances, the arene starting material is unavailable or difficult to obtain. In other instances, the directing effects of groups on the arene are such that the desired nitro compound is a minor product, or is not produced at all, in the nitration reaction. For example, m-toluidine is important as an intermediate in dyes and agricultural chemicals; application to toluene of the nitration-reduction approach, however, yields a mixture of toluidines comprising only a small percentage of m-toluidine. Finally, conditions required for reduction of the nitro group to the corresponding primary amine may be incompatible with other functional groups contained in the intermediate nitro arene.

SUMMARY OF THE INVENTION

The present invention provides a method for the preparation of a wide range of primary arylamines. The arylamines are prepared in two efficient, straightforward transformations: 1) an activated aryl group and an imine group are combined, in the presence of a transition metal catalyst, under conditions wherein the transition metal catalyst catalyzes the formation of a carbon-nitrogen bond between the activated carbon of the arene and the imine nitrogen; and 2) the resulting N-aryl imine is transformed, via any of a number of standard protocols, to the primary arylamine. The aforementioned method may also be exploited in the preparation of vinylamines.

DETAILED DESCRIPTION OF THE INVENTION

The ability to provide an aryl amination synthesis scheme which can be carried out to produce primary arylamines, such as aniline, has broad application, especially in the agricultural and pharmaceutical industries, as well as in the polymer industry. The present invention provides improvements in, and relating to, amination reactions for a wide range of aryl groups.

As illustrated in the appended examples, imines may be employed as a surrogate for ammonia in transition metal-catalyzed aminations of activated aryls groups to provide a route to primary arylamines. The amination and subsequent deprotection proceed uniformly in high yields. The ketimine functionality of the N-aryl imines produced in the amination reaction may be retained as a means of masking the primary amine, and/or the ketimine adducts may be isolated, e.g, by recrystallization and/or chromatography.

One aspect of the present invention provides a transition metal catalyzed reaction for amination of activated aryl groups using imines as ammonia equivalents. In general, the reaction combines an activated aryl group and an imine group with a transition metal catalyst under conditions wherein the transition metal catalyst catalyzes the coupling of the aryl and imine groups through the imine nitrogen. Either or both of the aryl and imine groups can be provided in reactive form, or as precursors which can be converted to the active form(s) under the reaction conditions. The aryl and imine groups may be on separate molecules (for an intermolecular amination), or may be contained in the same molecule (for an intramolecular amination).

In certain preferred embodiments, the subject reaction between an activated aryl group and an imine can be represented by the generalized reaction depicted in Scheme 1:

Scheme 1

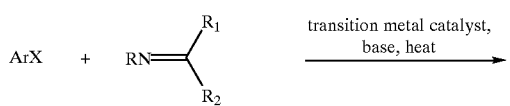

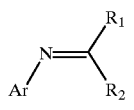

wherein:
Ar is selected from the set comprising optionally substituted monocyclic and polycyclic aromatic and heteroaromatic moieties;
X is selected from the set comprising Cl, Br, I, —OS(O)$_2$halogen, —OS(O)$_2$alkyl, and —OS(O)$_2$aryl;
the transition metal catalyst comprises a transition metal selected from Groups 5–12 of the periodic table;
R is selected from the set comprising hydrogen, trialkylstannyl, triarylstannyl, trialkylsilyl, triarylsilyl, lithium, sodium, potassium, magnesium halide, calcium halide, —B(OH)$_2$, groups that are replaced by hydrogen under the reaction conditions, and the like;
$R_1$ and $R_2$, each independently represent hydrogen, or an optionally substituted alkyl, alkenyl, alkynyl, heteroalkyl, aryl, heteroaryl, arylalkyl, or heteroarylalkyl group, or —(CH$_2$)$_m$—R$_8$; or $R_1$ and $R_2$ taken together form an optionally substituted ring;
the base is selected from the set comprising alkoxides, carbonates, amides, phosphates, fluorides, and the like;
$R_8$ represents an optionally substituted aryl, cycloalkyl, cycloalkenyl, heterocycle or polycycle; and
m is an integer in the range of 0 to 8 inclusive.

In preferred embodiments, $R_1$ and $R_2$ are not both hydrogen, and in even more preferred embodiments, neither $R_1$ nor $R_2$ is hydrogen.

In certain embodiments, the base is selected from the set comprising alkoxides and carbonates.

In certain preferred embodiments, the base is sodium tert-butoxide or cesium carbonate.

The reaction is run in the presence of at least a catalytic amount of a transition metal catalyst which catalyzes the reaction between the imine and activated aryl nucleus. Further guidance for selecting these components is provided below and in the Examples.

The resulting N-aryl imine products may be transformed to a primary amine group (see Scheme 2).

Scheme 2

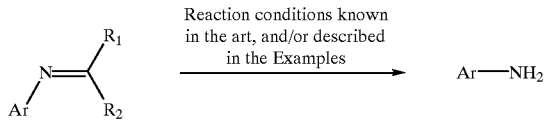

The subject amination reaction can be used as part of a combinatorial synthesis scheme to yield aryl amines (for a discussion of combinatorial libraries and methods, see: Section V). Accordingly, another aspect of the present invention relates to use of the subject method to generate variegated libraries of aryl amines of the general formula Ar—NH$_2$ and/or aryl ketimines of the general formula Ar—N=C(R$_1$)R$_2$, and to the libraries themselves. The libraries may be soluble or linked to insoluble supports, e.g., either through substituents of the aryl group or through $R_1$ or $R_2$ in the case of libraries derived with the imine intact, the latter providing a convenient means to cleave the aryl amines from the support.

In certain embodiments, the subject method can be used to generate vinyl amines.

In certain preferred embodiments, the subject reaction between an activated vinyl group and an imine can be represented by the generalized reaction depicted in Scheme 3:

Scheme 3

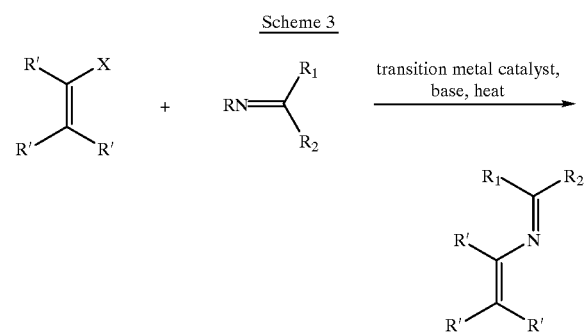

wherein:
X is selected from the set comprising Cl, Br, I, —OS(O)$_2$halogen, —OS(O)$_2$alkyl, and —OS(O)$_2$aryl;
the transition metal catalyst comprises a transition metal selected from Groups 5–12 of the periodic table;
R is selected from the set comprising hydrogen, trialkylstannyl, triarylstannyl, trialkylsilyl, triarylsilyl, lithium, sodium, potassium, magnesium halide, calcium halide, —B(OH)$_2$, groups that are replaced by hydrogen under the reaction conditions, and the like;
$R_1$ and $R_2$, each independently represent hydrogen, or an optionally substituted alkyl, alkenyl, alkynyl, heteroalkyl, aryl, heteroaryl, arylalkyl, or heteroarylalkyl group, or —(CH$_2$)$_m$—R$_8$; or $R_1$ and $R_2$ taken together form an optionally substituted ring;
R' is selected, independently for each occurrence, and as valence and stability permit, from the set comprising hydrogen, halogen, alkyl, alkenyl, alkynyl, heteroalkyl, aryl, heteroaryl, arylalkyl, heteroarylalkyl, formyl, acyl, amino, acylamino, amido, amidino, cyano, nitro, sulfonyl, sulfoxido, sulfate, sulfonate, sulfamoyl, sulfonamido, phosphoryl, phosphonate, phosphinate, —(CH$_2$)$_m$—R$_8$, —(CH$_2$)$_m$—OH, —(CH$_2$)$_m$—O-alkyl, —(CH$_2$)$_m$—O-alkenyl, —(CH$_2$)$_m$—O-aryl, —(CH$_2$)$_m$(CH$_2$)$_m$—R$_8$, —(CH$_2$)$_m$—SH, —(CH$_2$)$_m$—S-alkyl, —(CH$_2$)$_m$—S-alkenyl, —(CH$_2$)$_m$—S-aryl, —(CH$_2$)$_m$—S—(CH$_2$)$_m$—R$_8$, a solid support, a polymeric support, and the like;
the base is selected from the set comprising alkoxides, carbonates, amides, phosphates, fluorides, and the like;
$R_8$ represents an optionally substituted aryl, cycloalkyl, cycloalkenyl, heterocycle or polycycle; and
m, independently for each occurrence, is an integer in the range of 0 to 8 inclusive.

In preferred embodiments, $R_1$ and $R_2$ are not both hydrogen, and in even more preferred embodiments, neither $R_1$ or $R_2$ are hydrogen. As above, the imine can be provided in the form of a precursor which is tranformed in situ to the reactive imine or its equivalent.

In certain embodiments, R' is selected, independently for each occurrence, from the set comprising optionally substituted alkyl, heteroalkyl, aryl, heteroaryl, arylalkyl, heteroarylalkyl, alkenyl, and alkynyl groups; any two instances of R', taken together, and subject to art-recognized geometric constraints, may form a ring comprising between three and about fifteen backbone atoms.

In certain embodiments, the base is selected from the set comprising alkoxides and carbonates.

In certain preferred embodiments, the base is sodium tert-butoxide or cesium carbonate.

The reaction is run in the presence of at least a catalytic amount of a transition metal catalyst which catalyzes the reaction between the imine and activated vinyl nucleus. Further guidance for selecting these components is provided below and in the Examples.

I. Definitions

For convenience, before further description of the present invention, certain terms employed in the specification, examples, and appended claims are collected here.

The term "substrate aryl group" refers to an aryl group containing an electrophilic atom which is susceptible to the subject cross-coupling reaction, e.g., the electrophilic atom bears a leaving group. In reaction scheme 1, the substrate aryl is represented by ArX, and X is the leaving group. The aryl group, Ar, is said to be substituted if, in addition to X, it is substituted at yet other positions. The substrate aryl group can be a single ring molecule, or can be a substituent of a larger molecule.

The term "reactive imine group" refers to a ketimine group which can attack the electrophilic atom of the substrate aryl group and replace the leaving group in the subject cross-coupling reaction. In Scheme 1, the imine reactant is represented by $RN=C(-R_1)-R_2$. The reactive imine group can be a separate molecule from the substrate aryl group, or a substituent of the same molecule (e.g., for intramolecular embodiments).

The term "nucleophile" is recognized in the art, and as used herein means a chemical moiety having a reactive pair of electrons.

The term "electrophile" is art-recognized and refers to chemical moieties which can accept a pair of electrons from a nucleophile as defined above, or from a Lewis base. Electrophilic moieties useful in the method of the present invention include halides and sulfonates.

The terms "electrophilic atom", "electrophilic center" and "reactive center" as used herein refer to the atom of the substrate aryl moiety which is attacked by, and forms a new bond to, the imine nitrogen. In most cases, but not all, this will also be the aryl ring atom from which the leaving group departs.

The term "electron-withdrawing group" is recognized in the art, and denotes the tendency of a substituent to attract valence electrons from neighboring atoms, i.e., the substituent is electronegative with respect to neighboring atoms. A quantification of the level of electron-withdrawing capability is given by the Hammett sigma (σ) constant. This well known constant is described in many references, for instance, J. March, *Advanced Organic Chemistry*, McGraw Hill Book Company, New York, (1977 edition) pp. 251–259. The Hammett constant values are generally negative for electron donating groups ($\sigma[P]=-0.66$ for $NH_2$) and positive for electron withdrawing groups ($\sigma[P]=0.78$ for a nitro group), σ[P] indicating para substitution. Exemplary electron-withdrawing groups include nitro, ketone, aldehyde, sulfonyl, trifluoromethyl, —CN, chloride, and the like. Exemplary electron-donating groups include amino, methoxy, and the like.

The term "reaction product" means a compound which results from the reaction of the ketimine and the substrate aryl group. in general, the term "reaction product" will be used herein to refer to a stable, isolable N-aryl imine, or primary aryl amine derived therefrom, and not to unstable intermediates or transition states.

The term "catalytic amount" is recognized in the art and means a substoichiometric amount of a reagent relative to a reactant. As used herein, a catalytic amount means from 0.0001 to 90 mole percent reagent relative to a reactant, more preferably from 0.001 to 50 mole percent, still more preferably from 0.01 to 10 mole percent, and even more preferably from 0.1 to 5 mole percent reagent to reactant.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In preferred embodiments, a straight chain or branched chain alkyl has 30 or fewer carbon atoms in its backbone (e.g., $C_1$–$C_{30}$ for straight chain, $C_3$–$C_{30}$ for branched chain), and more preferably 20 or fewer. Likewise, preferred cycloalkyls have from 3–10 carbon atoms in their ring structure, and more preferably have 5, 6 or 7 carbons in the ring structure.

Moreover, the term "alkyl" (or "lower alkyl") as used throughout the specification and claims is intended to include both "unsubstituted alkyls" and "substituted alkyls", the latter of which refers to alkyl moieties having substituents replacing a hydrogen on one or more carbons of the hydrocarbon backbone. Such substituents can include, for example, a halogen, a hydroxyl, a carbonyl (such as a carboxyl, an ester, a formyl, or a ketone), a thiocarbonyl (such as a thioester, a thioacetate, or a thioformate), an alkoxyl, a phosphoryl, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like.

The term "aralkyl", as used herein, refers to an alkyl group substituted with an aryl group (e.g., an aromatic or heteroaromatic group).

The terms "alkenyl" and "alkynyl" refer to unsaturated aliphatic groups analogous in length and possible substitution to the alkyls described above, but that contain at least one double or triple bond, respectively.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Preferred alkyl groups are lower alkyls. In preferred embodiments, a substituent designated herein as alkyl is a lower alkyl.

The term "aryl" as used herein includes 5-, 6- and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics". The aromatic ring can be substituted at one or more ring positions with such substituents as described above, for example, halogen, azide, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —CF$_3$, —CN, or the like. The term "aryl" also includes polycyclic ring systems having two or more rings in which two or more carbons are common to two adjoining rings (the rings are "fused") wherein at least one of the rings is aromatic, e.g., the other rings can be cycloalkyls, cycloalkenyls, cycloalkenyls, aryls and/or heterocyclyls.

The terms "heterocyclyl" or "heterocyclic group" refer to 3- to 10-membered ring structures, more preferably 3- to 7-membered rings, whose ring structures include one to four heteroatoms. Heterocycles can also be polycycles. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, perimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —CF$_3$, —CN, or the like.

The terms "polycyclyl" or "polycyclic group" refer to two or more rings (e.g., cycloalkyls, cycloalkenyls, cycloalkenyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —CF$_3$, —CN, or the like.

The term "carbocycle", as used herein, refers to an aromatic or non-aromatic ring in which each atom of the ring is carbon.

The term "heteroatom" as used herein means an atom of any element other than carbon or hydrogen. Preferred heteroatoms are nitrogen, oxygen, sulfur and phosphorous.

As used herein, the term "nitro" means —NO$_2$; the term "halogen" designates —F, —Cl, —Br or —I; the term "sulfhydryl" means —SH; the term "hydroxyl" means —OH; and the term "sulfonyl" means —SO$_2$—.

The terms "amine" and "amino" are art recognized and refer to both unsubstituted and substituted amines, e.g., a moiety that can be represented by the general formula:

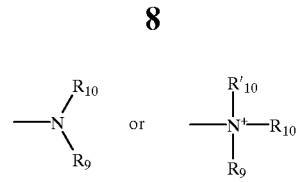

wherein $R_9$, $R_{10}$ and $R'_{10}$ each independently represent a hydrogen, an alkyl, an alkenyl, —(CH$_2$)$_m$—R$_8$, or $R_9$ and $R_{10}$ taken together with the N atom to which they are attached complete a heterocycle having from 4 to 8 atoms in the ring structure; $R_8$ represents an aryl, a cycloalkyl, a cycloalkenyl, a heterocycle or a polycycle; and m is zero or an integer in the range of 1 to 8. In preferred embodiments, only one of $R_9$ or $R_{10}$ can be a carbonyl, e.g., $R_9$, $R_{10}$ and the nitrogen together do not form an imide. In even more preferred embodiments, $R_9$ and $R_{10}$ (and optionally $R'_{10}$) each independently represent a hydrogen, an alkyl, an alkenyl, or —(CH$_2$)$_m$—R$_8$. Thus, the term "alkylamine" as used herein means an amine group, as defined above, having a substituted or unsubstituted alkyl attached thereto, i.e., at least one of $R_9$ and $R_{10}$ is an alkyl group.

The term "acylamino" is art-recognized and refers to a moiety that can be represented by the general formula:

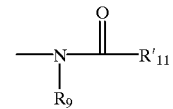

wherein $R_9$ is as defined above, and $R'_{11}$ represents a hydrogen, an alkyl, an alkenyl or —(CH$_2$)$_m$—R$_8$, where m and $R_8$ are as defined above.

The term "amido" is art recognized as an amino-substituted carbonyl and includes a moiety that can be represented by the general formula:

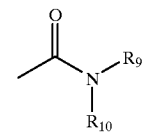

wherein $R_9$, $R_{10}$ are as defined above. Preferred embodiments of the amide will not include imides which may be unstable.

The term "alkylthio" refers to an alkyl group, as defined above, having a sulfur radical attached thereto. In preferred embodiments, the "alkylthio" moiety is represented by one of —S-alkyl, —S-alkenyl, —S-alkynyl, and —S—(CH$_2$)$_m$—R$_8$, wherein m and $R_8$ are defined above. Representative alkylthio groups include methylthio, ethylthio, and the like.

The term "carbonyl" is art recognized and includes such moieties as can be represented by the general formula:

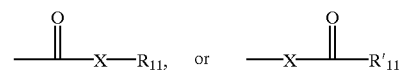

wherein X is a bond or represents an oxygen or a sulfur, and $R_{11}$ represents a hydrogen, an alkyl, an alkenyl, —(CH$_2$)$_m$—R$_8$ or a pharmaceutically acceptable salt, $R'_{11}$ represents a hydrogen, an alkyl, an alkenyl or —(CH$_2$)$_m$—R$_8$, where m and $R_8$ are as defined above. Where X is an oxygen and $R_{11}$ or $R'_{11}$ is not hydrogen, the formula represents an "ester".

Where X is an oxygen, and $R_{11}$ is as defined above, the moiety is referred to herein as a carboxyl group, and particularly when $R_{11}$ is a hydrogen, the formula represents a "carboxylic acid". Where X is an oxygen, and $R'_{11}$ is hydrogen, the formula represents a "formate". In general, where the oxygen atom of the above formula is replaced by sulfur, the formula represents a "thiolcarbonyl" group. Where X is a sulfur and $R_{11}$ or $R'_{11}$ is not hydrogen, the formula represents a "thiolester." Where X is a sulfur and $R_{11}$ is hydrogen, the formula represents a "thiolcarboxylic acid." Where X is a sulfur and $R_{11}'$ is hydrogen, the formula represents a "thiolformate." On the other hand, where X is a bond, and $R_{11}$ is not hydrogen, the above formula represents a "ketone" group. Where X is a bond, and $R_{11}$ is hydrogen, the above formula represents an "aldehyde" group.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, —O-alkynyl, —O—$(CH_2)_m$—$R_8$, where m and $R_8$ are described above.

The term "sulfonate" is art recognized and includes a moiety that can be represented by the general formula:

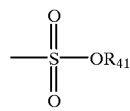

in which $R_{41}$ is an electron pair, hydrogen, alkyl, cycloalkyl, or aryl.

The term "sulfate" is art recognized and includes a moiety that can be represented by the general formula:

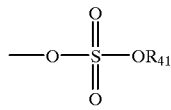

in which $R_{41}$ is as defined above.

The term "sulfonamido" is art recognized and includes a moiety that can be represented by the general formula:

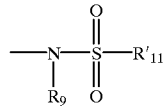

in which $R_9$ and $R'_{11}$ are as defined above

The term "sulfamoyl" is art-recognized and includes a moiety that can be represented by the general formula:

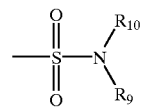

in which $R_9$ and $R_{10}$ are as defined above.

The terms "sulfoxido" or "sulfinyl", as used herein, refers to a moiety that can be represented by the general formula:

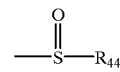

in which $R_{44}$ is selected from the group consisting of hydrogen, alkyl, alkenyl, alkynyl, cycloalkyl, heterocyclyl, aralkyl, or aryl.

A "phosphoryl" can in general be represented by the formula:

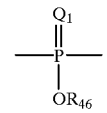

wherein $Q_1$ represented S or O, and $R_{46}$ represents hydrogen, a lower alkyl or an aryl. When used to substitute, e.g., an alkyl, the phosphoryl group of the phosphorylalkyl can be represented by the general formula:

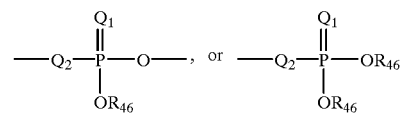

wherein $Q_1$ represented S or O, and each $R_{46}$ independently represents hydrogen, a lower alkyl or an aryl, $Q_2$ represents O, S or N. When $Q_1$ is an S, the phosphoryl moiety is a "phosphorothioate".

A "phosphoramidite" can be represented in the general formula:

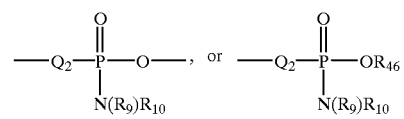

wherein $R_9$ and $R_{10}$ are as defined above, and $Q_2$ represents O, S or N.

A "phosphonamidite" can be represented in the general formula:

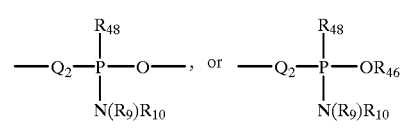

wherein $R_9$ and $R_{10}$ are as defined above, $Q_2$ represents O, S or N, and $R_{48}$ represents a lower alkyl or an aryl, $Q_2$ represents O, S or N.

A "selenoalkyl" refers to an alkyl group having a substituted seleno group attached thereto. Exemplary "selenoethers" which may be substituted on the alkyl are selected from one of —Se-alkyl, —Se-alkenyl, —Se-alkynyl, and —Se—$(CH_2)_m$—$R_7$, m and $R_7$ being defined above.

Analogous substitutions can be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

The abbreviations Me, Et, Ph, Tf, Nf, Ts, Ms, and dba represent methyl, ethyl, phenyl, trifluoromethanesulfonyl, nonafluorobutanesulfonyl, p-toluenesulfonyl, methanesulfonyl, and dibenzylideneacetone, respectively. A more comprehensive list of the abbreviations utilized by organic chemists of ordinary skill in the art appears in the first issue of each volume of the *Journal of Organic Chemistry*; this list is typically presented in a table entitled *Standard List of Abbreviations*. The abbreviations contained in said list, and all abbreviations utilized by organic chemists of ordinary skill in the art are hereby incorporated by reference.

The terms ortho, meta and para apply to 1,2-, 1,3- and 1,4-disubstituted benzenes, respectively. For example, the names 1,2-dimethylbenzene and ortho-dimethylbenzene are synonymous.

The phrase "protecting group" as used herein means temporary modifications of a potentially reactive functional group which protect it from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, 2$^{nd}$ ed.; Wiley: New York, 1991).

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described hereinabove. The permissible substituents can be one or more and the same or different for appropriate organic compounds. For purposes of this invention, the heteroatoms such as nitrogen may have hydrogen substituents and/or any permissible substituents of organic compounds described herein which satisfy the valencies of the heteroatoms. This invention is not intended to be limited in any manner by the permissible substituents of organic compounds.

A "polar solvent" means a solvent which has a dielectric constant ($\epsilon$) of 2.9 or greater, such as DMF, THF, ethylene glycol dimethyl ether (DME), DMSO, acetone, acetonitrile, methanol, ethanol, isopropanol, n-propanol, t-butanol or 2-methoxyethyl ether. Preferred solvents are DMF, DME, NMP, and acetonitrile.

A "polar, aprotic solvent" means a polar solvent as defined above which has no available hydrogens to exchange with the compounds of this invention during reaction, for example DMF, acetonitrile, diglyme, DMSO, or THF.

An "aprotic solvent" means a non-nucleophilic solvent having a boiling point range above ambient temperature, preferably from about 25° C. to about 190° C., more preferably from about 80° C. to about 160° C., most preferably from about 80° C. to 150° C., at atmospheric pressure. Examples of such solvents are acetonitrile, toluene, DMF, diglyme, THF or DMSO.

For purposes of this invention, the chemical elements are identified in accordance with the Periodic Table of the Elements, CAS version, Handbook of Chemistry and Physics, 67th Ed., 1986–87, inside cover. Also for purposes of this invention, the term "hydrocarbon" is contemplated to include all permissible compounds having at least one hydrogen and one carbon atom. In a broad aspect, the permissible hydrocarbons include acyclic and cyclic, branched and unbranched, carbocyclic and heterocyclic, aromatic and nonaromatic organic compounds which can be substituted or unsubstituted.

II. Substrates and Catalysts

As described above, one invention of the Applicants' features a general amination reaction that constitutes a novel route to primary aryl and vinyl amines; said method comprises combining a imine with an aryl group (a "substrate aryl") having an electrophilic center susceptible to attack by the imine nitrogen. The reaction will also include at least a catalytic amount of a transition metal catalyst. The combination is maintained under conditions appropriate for the metal catalyst to catalyze the formation of a new carbon-nitrogen bond between the imine nitrogen and the electrophilic atom of the substrate aryl.

The substrate aryl compounds include compounds derived from simple aromatic rings (single or polycylic) such as benzene, naphthalene, anthracene and phenanthrene; or heteroaromatic rings (single or polycylic), such as pyrrole, thiophene, thianthrene, flran, pyran, isobenzofuran, chromene, xanthene, phenoxathiin, pyrrole, imidazole, pyrazole, thiazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, perimidine, phenanthroline, phenazine, phenarsazine, phenothiazine, furazan, phenoxazine, pyrrolidine, oxolane, thiolane, oxazole, piperidine, piperazine, morpholine and the like.

Suitable aromatic compounds may have the formula $Z_p\text{ArX}$, where X is an activated substituent. An activated substituent, X, is characterized as being a good leaving group. In general, the leaving group is a group such as a halide or sulfonate. For the purposes of the present invention, an activated substituent is typically a moiety whose conjugate acid, HX, has a pKa of less than 5.0. Suitable activated substituents include, by way of example only, halides such as chloride, bromide and iodide, and sulfonates, such as triflate, mesylate and tosylate. In preferred embodiments, the leaving group is iodide, bromide, or a sulfonate. Chloride and fluoride may also serve as leaving groups, though other electronegative substitution on the aryl group may be required to activate these halogens as leaving groups in the subject metal catalyzed reactions.

In aromatic compounds corresponding to the formula $Z_p\text{ArX}$, Z represents one or more optional substituents on the aromatic ring, though each occurence of Z (p>1) is independently selected. By way of example only, each incidence of substitution independently can be, as valence and stability permit, a halogen, a lower alkyl, a lower alkenyl, a lower alkynyl, a carbonyl (e.g., an ester, a carboxylate, or a formate), a thiocarbonyl (e.g., a thiolester, a thiolcarboxylate, or a thiolformate), a ketyl, an aldehyde, an amino, an acylamino, an amido, an amidino, a cyano, a nitro, an azido, a sulfonyl, a sulfoxido, a sulfate, a sulfonate, a sulfamoyl, a sulfonamido, a phosphoryl, a phosphonate, a phosphinate, $-(CH_2)_m-R_8$, $-(CH_2)_m-OH$, $-(CH_2)_m-$O-lower alkyl, $-(CH_2)_m-$O-lower alkenyl, $-(CH_2)_m-$O$-(CH_2)_n-R_8$, $-(CH_2)_m-SH$, $-(CH_2)_m-$S-lower alkyl, $-(CH_2)_m-$S-lower alkenyl, $-(CH_2)_m-S-(CH_2)_n-R_8$, or protecting groups of the above or a solid or polymeric support; $R_8$ represents a substituted or unsubstituted aryl, aralkyl, cycloalkyl, cycloalkenyl, or heterocycle;

and n and m are independently for each occurrence zero or an integer in the range of 1 to 6. P is preferably in the range of 0 to 5. For fused rings, where the number of substitution sites on the aryl group increases, p may be adjusted appropriately.

A wide variety of substrate aryl groups are useful in the methods of the present invention. The choice of substrate will depend on factors such as the imine to be employed and the desired product, and an appropriate aryl substrate will be apparent to the skilled artisan. It will be understood that the aryl substrate preferably will not contain any functional groups that interfere with the subject reaction. It will further be understood that not all activated aryl substrates will react with every imine.

The reactive imine group can be comprised by a separate molecule, from the standpoint of the substrate aryl group, or can be comprised by the same molecule (e.g., for intramolecular embodiments). The reactive ketimine group which is used in the subject coupling reaction can be represented by general formula $RN=C(-R_1)-R_2$, wherein $R_1$ and $R_2$ are defined above. In certain embodiments, one or both of $R_1$ and $R_2$ are linked to a solid support. In other embodiments, $R_1$ and $R_2$ taken together form a ring, e.g., such as in cyclohexanimine.

In certain embodiments, the imine is generated in situ, e.g., by conversion of a precursor under the reaction conditions. For instance, the addition of organometallic reagents, such as organolithium compounds or Grignard reagents, to nitriles usually gives imine salts (Layer, (1963) Chem. Rev. 63:489; "Chemistry of the Carbon-Nitrogen Double Bond," S. Patai, Ed. Interscience, New York, N.Y., 1970, chapters 6–8). Thus, the imine can be derived from a nitrile precursor, e.g., by addition of an alkyllithium, aryllithium,

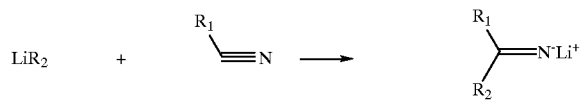

or a Grignard reagent, such as alkylmagnesium halide or arylmagnesium halide, to produce an imine salt.

In certain embodiments, the reactive imine is an imine of a ketone, rather than of formaldehyde or an aldehyde, in order to obviate β-elimination of a hydrogen at the imine carbon. In preferred embodiments, the selection of $R_1$ and $R_2$ provides a relatively unhindered methanimine core. Other criteria for selecting the reactive may imine include: cost; reactivity (e.g., efficiency of reaction); the stability of the ketimine under the reaction conditions; the solubility of the imine reactant and/or imine product under the reaction conditions; the reaction conditions required for tranformation of the ketimine to the primary amine, e.g., based on the compatibility of other substituents on the aryl group; the use of the imine group to attach the product to a soluble support; and the crystallinity conferred on the product for purification.

As suitable, the catalysts employed in the subject method involve the use of metals which can mediate amination of the aryl groups ArX by the ketimine as defined above. In general, catalysts intended by the present invention can be characterized in terms of a number of features. For instance, the metal should be capable of activating the imine for attack on an electrophilic center of the substrate aryl.

In general, any transition metal (e.g., having d electrons) may be used to form the catalyst, e.g., a metal selected from one of Groups 3–12 of the periodic table or from the lanthanide series. However, in preferred embodiments, the metal will be selected from the group of late transition metals, e.g. preferably from Groups 5–12 and even more preferably Groups 8–10. For example, suitable metals include platinum, palladium, iron, nickel, ruthenium and rhodium. The particular form of the metal to be used in the reaction is selected to provide, under the reaction conditions, metal centers which are coordinately unsaturated and not in their highest oxidation state. The metal core of the catalyst should be a zero-valent transition metal, such as Pd or Ni with the ability to undergo oxidative addition to the Ar—X bond. The zero-valent state, $M^0$, may be generated in situ from $M^{+2}$.

To further illustrate, suitable transition metal catalysts include soluble or insoluble complexes of platinum, palladium and nickel. Nickel and palladium are particularly preferred and palladium is most preferred. A zero-valent metal center is presumed to participate in the catalytic carbon-heteroatom or carbon-carbon bond forming sequence. Thus, the metal center is desirably in the zero-valent state or is capable of being reduced to metal(0). Suitable soluble palladium complexes include, but are not limited to, tris(dibenzylideneacetone) dipalladium [$Pd_2(dba)_3$], bis(dibenzylideneacetone) palladium [$Pd(dba)_2$] and palladium acetate. Alternatively, particularly for nickel catalysts, the active species for the oxidative-addition step may be the metal (+1) oxidation state.

Catalyst complexes may comprise chelating ligands, such as by way of example only, alkyl and aryl derivatives of phosphines and bisphosphines, imines, arsines, and hybrids thereof, including hybrids of phosphines with amines. Weakly or non-nucleophilic stabilizing ions are preferred to avoid complicating side reaction of the counter ion attacking or adding to the electrophilic center of the substrate aryl. Additionally, heterogeneous catalysts containing forms of these elements are also suitable catalysts for any of the transition metal catalyzed reactions of the present invention. Catalysts containing palladium and nickel are preferred. It is expected that these catalysts will perform comparably because they are known to undergo similar reactions, namely cross-coupling reactions, which are may be involved in the formation of the arylamines of the present invention.

The coupling can be catalyzed by a palladium catalyst which may be derived from, to illustrate, $PdCl_2$, $PdOAc_2$, $(CH_3CN)_2PdCl_2$, $Pd[P(C_6H_5)]_4$, and polymer supported Pd(0). In other embodiments, the reaction can be catalyzed by a nickel catalyst which may be derived from, to illustrate only, $Ni(acac)_2$, $Ni(COD)_2$, $NiCl_2[P(C_6H_5)]_2$, Raney nickel and the like, wherein "acac" represents acetylacetonate.

The active form of the transition metal catalyst is not well characterized. Therefore, it is contemplated that the "transition metal catalyst" of the present invention, as that term is used herein, shall include any transition metal catalyst and/or catalyst precursor as it is introduced into the reaction vessel and which is, if necessary, converted in situ into the active phase, as well as the active form of the catalyst which participates in the reaction. The transition metal catalyst is present in catalytic amounts relative to the substrate aryl, e.g., preferably in the range of 0.01 to 10 mole percent, and more preferably 1.0 to 2.5 mol %, with respect to the aromatic compound.

In some instances, it may be necessary to include additional reagents in the reaction to promote reactivity of either the transition metal catalyst or activated aryl nucleus. In particular, it may be advantageous to include a suitable base such as, for example: an alkoxides such as sodium tert-butoxide, an alkali metal amide such as sodium amide, lithium diisopropylamide or an alkali metal bis(trialkyl-silyl)amides, e.g., such as lithium bis-(trimethyl-silyl)amide or sodium bis-(trimethyl-silyl)amide, a tertiary amine (e.g. triethylamine, trimethylamine, N,N-dimethylaminopyridine, 1,5-diazabicycl[4.3.0]nonene-5 (DBN), 1,5-diazabicycl [5.4.0]undecene-5 (DBU), alkali, alkaline earth carbonate, bicarbonate or hydroxide (e.g. sodium, magnesium, calcium, barium, potassium, or cesium carbonate, hydroxide or bicarbonate). Preferred bases include $Cs_2CO_3$ and DBU.

In certain embodiments of the subject method, the transition metal catalyst includes one or more phosphine ligands, e.g., as a Lewis base that influences the stability and electronic properties of the transition metal catalyst, and/or stabilizes organometallic intermediates. Phosphine ligands are commercially available or can be prepared by methods similar to processes known per se. The phosphines can be monodentate phosphine ligands, such as, but not limited to, trimethylphosphine, triethylphosphine, tripropylphosphine, triisopropylphosphine, tributylphosphine, tricyclohexylphosphine, trimethyl phosphite, triethyl phosphite, tripropyl phosphite, triisopropyl phosphite, tributyl phosphite and tricyclohexyl phosphite, in particular triphenylphosphine, tri(o-tolyl)phosphine, triisopropylphosphine or tricyclohexylphosphine; or a bidentate phosphine ligand such as 2,2'-bis(diphenylphosphino)-1,1'-binaphthyl (BINAP), 1,2-bis(dimethylphosphino)ethane, 1,2-bis(diethylphosphino)ethane, 1,2-bis(dipropylphosphino)ethane, 4,5-bis(diphenylphosphino)-9,9-dimethylxanthene (xant-phos), 1,1'-bis(diphenylphosphino)ferrocene (dppf), bis(2-(diphenylphosphino)phenyl)ether [DPE-phos], 1,2-bis(diisopropylphosphino)ethane, 1,2-bis(dibutyl-phosphino)ethane, 1,2-bis(dicyclohexylphosphino)ethane, 1,3-bis(dicyclohexylphosphino)propane, 1,3-bis(diisopropylphosphino)propane, 1,4-bis(diisopropylphosphino)-butane and 2,4-bis(dicyclohexylphosphino)pentane. Ligands comprising Lewis basic nitrogen atoms may be included in the transition metal catalyst, e.g., 1,10-phenanthroline and the like.

III. Exemplary Catalyzed Reactions

The present invention enables the preparation of a wide range of primary arylamines. The reaction can be accomplished using a wide range of ketimines, which are either commercially available or readily obtainable using a variety of methods known in the art.

Thus, for example, the subject methods can be used, in addition to the reactions detailed in the appended examples, in such exemplary synthetic schemes as shown below.

As an illustrative embodiment, the subject method may exploited in the synthesis of amino thiazoles; this class of compound finds use in the area of markers for mineral oils.

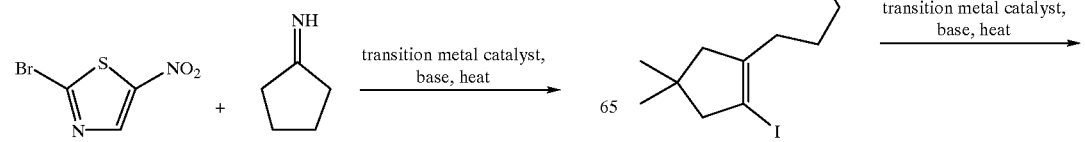

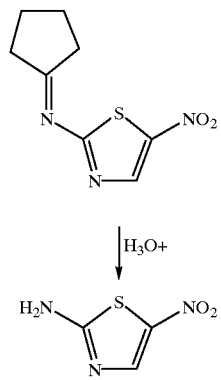

In a second illustrative embodiment, the subject method is exploited in the installation of an amino group on a benzene ring bearing an olefin-containing substituent; this substituent would likely be incompatible with hydrogenation conditions.

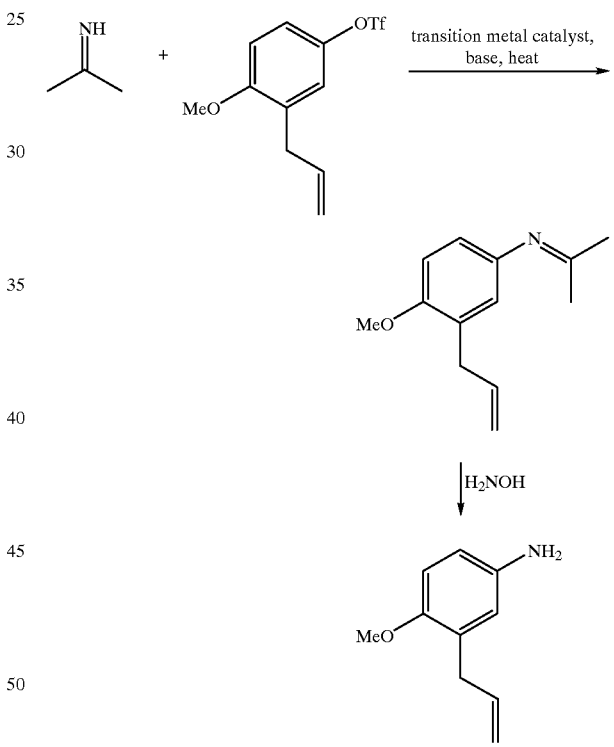

In an additional illustrative embodiment, the subject method provides a 2-aza-bicyclo[5.3.1]decadiene.

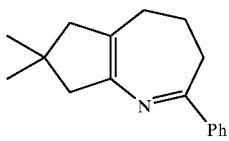

The following illustrative embodiment highlights the chemoselectivity available with the methods of the present invention.

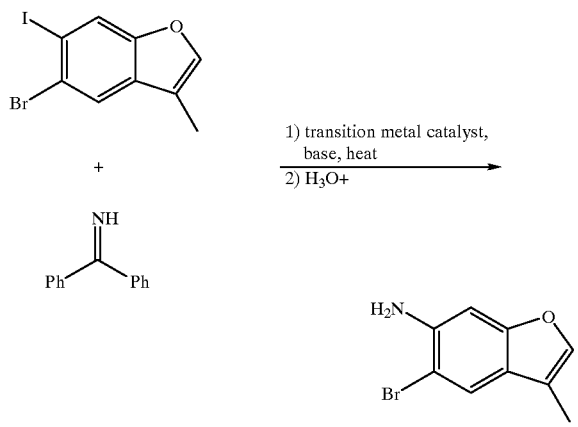

In another illustrative embodiment, the use of the subject method, in an intramolecular sense, yields a dihydroquinoline, which upon oxidation, will provide a quinoline.

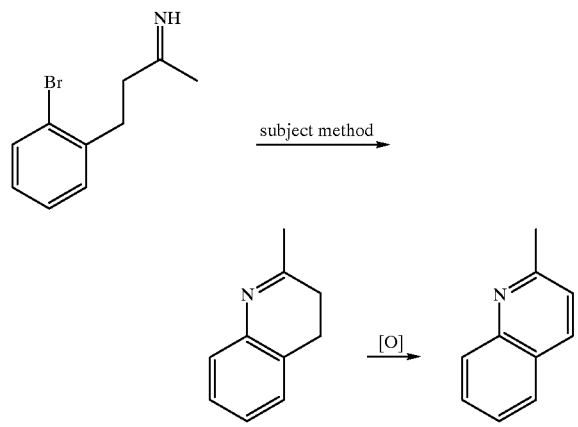

As is clear from the above discussion, the products which may be produced by the amination reaction of this invention can undergo further reaction(s) to afford desired derivatives thereof. Such permissible derivatization reactions can be carried out in accordance with conventional procedures known in the art. For example, potential derivatization reactions include esterification, oxidation of alcohols to aldehydes and acids, N-alkylation of amides, nitrile reduction, acylation of ketones by esters, acylation of amines and the like.

IV. Reaction Conditions

The reactions of the present invention may be performed under a wide range of conditions, though it will be understood that the solvents and temperature ranges recited herein are not limitative and only correspond to a preferred mode of the process of the invention.

In general, it will be desirable that reactions are run using mild conditions which will not adversely affect the reactants, the catalyst, or the product. For example, the reaction temperature influences the speed of the reaction, as well as the stability of the reactants and catalyst. The reactions will usually be run at temperatures in the range of 25° C. to 300° C., more preferably in the range 25° C. to 150° C.

In general, the subject reactions are carried out in a liquid reaction medium. The reactions may be run without addition of solvent. Alternatively, the reactions may be run in an inert solvent, preferably one in which the reaction ingredients, including the catalyst, are substantially soluble. Suitable solvents include ethers such as diethyl ether, 1,2-dimethoxyethane, diglyme, t-butyl methyl ether, tetrahydrofuran and the like; halogenated solvents such as chloroform, dichloromethane, dichloroethane, chlorobenzene, and the like; aliphatic or aromatic hydrocarbon solvents such as benzene, xylene, toluene, hexane, pentane and the like; esters and ketones such as ethyl acetate, acetone, and 2-butanone; polar aprotic solvents such as acetonitrile, dimethylsulfoxide, dimethylformamide and the like; or combinations of two or more solvents.

The invention also contemplates reaction in a biphasic mixture of solvents, in an emulsion or suspension, or reaction in a lipid vesicle or bilayer. In certain embodiments, it may be preferred to perform the catalyzed reactions in the solid phase with one of the reactants anchored to a solid support.

In certain embodiments it is preferable to perform the reactions under an inert atmosphere of a gas such as nitrogen or argon.

The reaction processes of the present invention can be conducted in continuous, semi-continuous or batch fashion and may involve a liquid recycle operation as desired. The processes of this invention are preferably conducted in batch fashion. Likewise, the manner or order of addition of the reaction ingredients, catalyst and solvent are also not generally critical to the success of the reaction, and may be accomplished in any conventional fashion. In a order of events that, in some cases, can lead to an enhancement of the reaction rate, the base, e.g. t-BuONa, is the last ingredient to be added to the reaction mixture.

The reaction can be conducted in a single reaction zone or in a plurality of reaction zones, in series or in parallel or it may be conducted batchwise or continuously in an elongated tubular zone or series of such zones. The materials of construction employed should be inert to the starting materials during the reaction and the fabrication of the equipment should be able to withstand the reaction temperatures and pressures. Means to introduce and/or adjust the quantity of starting materials or ingredients introduced batchwise or continuously into the reaction zone during the course of the reaction can be conveniently utilized in the processes especially to maintain the desired molar ratio of the starting materials. The reaction steps may be effected by the incremental addition of one of the starting materials to the other. Also, the reaction steps can be combined by the joint addition of the starting materials to the metal catalyst. When complete conversion is not desired or not obtainable, the starting materials can be separated from the product and then recycled back into the reaction zone.

The processes may be conducted in either glass lined, stainless steel or similar type reaction equipment. The reaction zone may be fitted with one or more internal and/or external heat exchanger(s) in order to control undue temperature fluctuations, or to prevent any possible "runaway" reaction temperatures.

Furthermore, one or more of the reactants can be immobilized or incorporated into a polymer or other insoluble matrix by, for example, derivatization with one or more of substituents of the aryl group.

V. Combinatorial Libraries

The subject reactions readily lend themselves to the creation of combinatorial libraries of compounds for the screening of pharmaceutical, agrochemical or other biological or medically-related activity or material-related qualities. A combinatorial library for the purposes of the present invention is a mixture of chemically related compounds which may be screened together for a desired property; said libraries may be in solution or covalently linked to a solid support. The preparation of many related compounds in a single reaction greatly reduces and simplifies the number of screening processes which need to be carried out. Screening for the appropriate biological, pharmaceutical, agrochemical or physical property may be done by conventional methods.

Diversity in a library can be created at a variety of different levels. For instance, the substrate aryl groups used in a combinatorial approach can be diverse in terms of the core aryl moiety, e.g., a variegation in terms of the ring structure, and/or can be varied with respect to the other substituents.

A variety of techniques are available in the art for generating combinatorial libraries of small organic molecules. See, for example, Blondelle et al. (1995) *Trends Anal. Chem.* 14:83; the Affymax U.S. Pat. Nos. 5,359,115 and 5,362,899: the Ellman U.S. Pat. No. 5,288,514: the Still et al. PCT publication WO 94/08051; Chen et al. (1994) *JACS* 116:2661: Kerr et al. (1993) *JACS* 115:252; PCT publications WO92/10092, WO93/09668 and WO91/07087; and the Lerner et al. PCT publication WO93/20242). Accordingly, a variety of libraries on the order of about 16 to 1,000,000 or more diversomers can be synthesized and screened for a particular activity or property.

In an exemplary embodiment, a library of substituted diversomers can be synthesized using the subject reactions adapted to the techniques described in the Still et al. PCT publication WO 94/08051, e.g., being linked to a polymer bead by a hydrolyzable or photolyzable group, e.g., located at one of the positions of substrate. According to the Still et al. technique, the library is synthesized on a set of beads, each bead including a set of tags identifying the particular diversomer on that bead. In one embodiment, which is particularly suitable for discovering enzyme inhibitors, the beads can be dispersed on the surface of a permeable membrane, and the diversomers released from the beads by lysis of the bead linker. The diversomer from each bead will diffuse across the membrane to an assay zone, where it will interact with an enzyme assay. Detailed descriptions of a number of combinatorial methodologies are provided below.

Direct Characterization

A growing trend in the field of combinatorial chemistry is to exploit the sensitivity of techniques such as mass spectrometry (MS), e.g., which can be used to characterize sub-femtomolar amounts of a compound, and to directly determine the chemical constitution of a compound selected from a combinatorial library. For instance, where the library is provided on an insoluble support matrix, discrete populations of compounds can be first released from the support and characterized by MS. In other embodiments, as part of the MS sample preparation technique, such MS techniques as MALDI can be used to release a compound from the matrix, particularly where a labile bond is used originally to tether the compound to the matrix. For instance, a bead selected from a library can be irradiated in a MALDI step in order to release the diversomer from the matrix, and ionize the diversomer for MS analysis.

B) Multipin Synthesis

The libraries of the subject method can take the multipin library format. Briefly, Geysen and co-workers (Geysen et al. (1984) *PNAS* 81:3998–4002) introduced a method for generating compound libraries by a parallel synthesis on polyacrylic acid-grated polyethylene pins arrayed in the microtitre plate format. The Geysen technique can be used to synthesize and screen thousands of compounds per week using the multipin method, and the tethered compounds may be reused in many assays. Appropriate linker moieties can also been appended to the pins so that the compounds may be cleaved from the supports after synthesis for assessment of purity and further evaluation (c.f., Bray et al. (1990) *Tetrahedron Lett* 31:5811–5814; Valerio et al. (1991) *Anal Biochem* 197:168–177; Bray et al. (1991) *Tetrahedron Lett* 32:6163–6166).

C) Divide-Couple-Recombine

In yet another embodiment, a variegated library of compounds can be provided on a set of beads utilizing the strategy of divide-couple-recombine (see, e.g., Houghten (1985) *PNAS* 82:5131–5135; and U.S. Pat. Nos. 4,631,211; 5,440,016; 5,480,971). Briefly, as the name implies, at each synthesis step where degeneracy is introduced into the library, the beads are divided into separate groups equal to the number of different substituents to be added at a particular position in the library, the different substituents coupled in separate reactions, and the beads recombined into one pool for the next iteration.

In one embodiment, the divide-couple-recombine strategy can be carried out using an analogous approach to the so-called "tea bag" method first developed by Houghten, where compound synthesis occurs on resin sealed inside porous polypropylene bags (Houghten et al. (1986) *PNAS* 82:5131–5135). Substituents are coupled to the compound-bearing resins by placing the bags in appropriate reaction solutions, while all common steps such as resin washing and deprotection are performed simultaneously in one reaction vessel. At the end of the synthesis, each bag contains a single compound.

D) Combinatorial Libraries by Light-Directed, Spatially Addressable Parallel Chemical Synthesis A scheme of combinatorial synthesis in which the identity of a compound is given by its locations on a synthesis substrate is termed a spatially-addressable synthesis. In one embodiment, the combinatorial process is carried out by controlling the addition of a chemical reagent to specific locations on a solid support (Dower et al. (1991) *Annu Rep Med Chem* 26:271–280; Fodor, S. P. A. (1991) *Science* 251:767; Pirrung et al. (1992) U.S. Pat. No. 5,143,854; Jacobs et al. (1994) *Trends Biotechnol* 12:19–26). The spatial resolution of photolithography affords miniaturization. This technique can be carried out through the use protection/deprotection reactions with photolabile protecting groups.

The key points of this technology are illustrated in Gallop et al. (1994) *J Med Chem* 37:1233–1251. A synthesis substrate is prepared for coupling through the covalent attachment of photolabile nitroveratryloxycarbonyl (NVOC) protected amino linkers or other photolabile linkers. Light is used to selectively activate a specified region of the synthesis support for coupling. Removal of the photolabile protecting groups by light (deprotection) results in activation of selected areas. After activation, the first of a set of amino acid analogs, each bearing a photolabile protecting group on the amino terminus, is exposed to the entire surface. Coupling only occurs in regions that were addressed by light in the preceding step. The reaction is stopped, the plates washed, and the substrate is again illuminated through a second mask, activating a different region for reaction with a second protected building block. The pattern of masks and the sequence of reactants define the products and their locations. Since this process utilizes photolithography techniques, the number of compounds that can be synthesized is limited only by the number of synthesis sites that can be addressed with appropriate resolution. The position of each compound is precisely known; hence, its interactions with other molecules can be directly assessed.

In a light-directed chemical synthesis, the products depend on the pattern of illumination and on the order of addition of reactants. By varying the lithographic patterns, many different sets of test compounds can be synthesized simultaneously; this characteristic leads to the generation of many different masking strategies.

E) Encoded Combinatorial Libraries

In yet another embodiment, the subject method utilizes a compound library provided with an encoded tagging system. A recent improvement in the identification of active compounds from combinatorial libraries employs chemical indexing systems using tags that uniquely encode the reaction steps a given bead has undergone and, by inference, the structure it carries. Conceptually, this approach mimics phage display libraries, where activity derives from expressed peptides, but the structures of the active peptides are deduced from the corresponding genomic DNA sequence. The first encoding of synthetic combinatorial libraries employed DNA as the code. A variety of other forms of encoding have been reported, including encoding with sequenceable bio-oligomers (e.g., oligonucleotides and peptides), and binary encoding with additional non-sequenceable tags.

1) Tagging With Sequenceable Bio-oligomers

The principle of using oligonucleotides to encode combinatorial synthetic libraries was described in 1992 (Brenner et al. (1992) PNAS 89:5381–5383), and an example of such a library appeared the following year (Needles et al. (1993) *PNAS* 90:10700–10704). A combinatorial library of nominally $7^7$ (=823,543) peptides composed of all combinations of Arg, Gln, Phe, Lys, Val, D-Val and Thr (three-letter amino acid code), each of which was encoded by a specific dinucleotide (TA, TC, CT, AT, TT, CA and AC, respectively), was prepared by a series of alternating rounds of peptide and oligonucleotide synthesis on solid support. In this work, the amine linking functionality on the bead was specifically differentiated toward peptide or oligonucleotide synthesis by simultaneously preincubating the beads with reagents that generate protected OH groups for oligonucleotide synthesis and protected $NH_2$ groups for peptide synthesis (here, in a ratio of 1:20). When complete, the tags each consisted of 69-mers, 14 units of which carried the code. The bead-bound library was incubated with a fluorescently labeled antibody, and beads containing bound antibody that fluoresced strongly were harvested by fluorescence-activated cell sorting (FACS). The DNA tags were amplified by PCR and sequenced, and the predicted peptides were synthesized. Following such techniques, compound libraries can be derived for use in the subject method, where the oligonucleotide sequence of the tag identifies the sequential combinatorial reactions that a particular bead underwent, and therefore provides the identity of the compound on the bead.

The use of oligonucleotide tags permits exquisitely sensitive tag analysis. Even so, the method requires careful choice of orthogonal sets of protecting groups required for alternating co-synthesis of the tag and the library member. Furthermore, the chemical lability of the tag, particularly the phosphate and sugar anomeric linkages, may limit the choice of reagents and conditions that can be employed for the synthesis of non-oligomeric libraries. In preferred embodiments, the libraries employ linkers permitting selective detachment of the test compound library member for assay.

Peptides have also been employed as tagging molecules for combinatorial libraries. Two exemplary approaches are described in the art, both of which employ branched linkers to solid phase upon which coding and ligand strands are alternately elaborated. In the first approach (Kerr J M et al. (1993) *J Am Chem Soc* 115:2529–2531), orthogonality in synthesis is achieved by employing acid-labile protection for the coding strand and base-labile protection for the compound strand.

In an alternative approach (Nikolaiev et al. (1993) *Pept Res* 6:161–170), branched linkers are employed so that the coding unit and the test compound can both be attached to the same functional group on the resin. In one embodiment, a cleavable linker can be placed between the branch point and the bead so that cleavage releases a molecule containing both code and the compound (Ptek et al. (1991) *Tetrahedron Lett* 32:3891–3894). In another embodiment, the cleavable linker can be placed so that the test compound can be selectively separated from the bead, leaving the code behind. This last construct is particularly valuable because it permits screening of the test compound without potential interference of the coding groups. Examples in the art of independent cleavage and sequencing of peptide library members and their corresponding tags has confirmed that the tags can accurately predict the peptide structure.

2) Non-sequenceable Tagging: Binary Encoding

An alternative form of encoding the test compound library employs a set of non-sequencable electrophoric tagging molecules that are used as a binary code (Ohlmeyer et al. (1993) *PNAS* 90:10922–10926). Exemplary tags are haloaromatic alkyl ethers that are detectable as their trimethylsilyl ethers at less than femtomolar levels by electron capture gas chromatography (ECGC). Variations in the length of the alkyl chain, as well as the nature and position of the aromatic halide substituents, permit the synthesis of at least 40 such tags, which in principle can encode $2^{40}$ (e.g., upwards of $10^{12}$) different molecules. In the original report (Ohlmeyer et al., supra) the tags were bound to about 1% of the available amine groups of a peptide library via a photocleavable o-nitrobenzyl linker. This approach is convenient when preparing combinatorial libraries of peptide-like or other amine-containing molecules. A more versatile system has, however, been developed that permits encoding of essentially any combinatorial library. Here, the compound would be attached to the solid support via the photocleavable linker and the tag is attached through a catechol ether linker via carbene insertion into the bead matrix (Nestler et al. (1994) *J Org Chem* 59:4723–4724). This orthogonal attachment strategy permits the selective detachment of library members for assay in solution and subsequent decoding by ECGC after oxidative detachment of the tag sets.

Although several amide-linked libraries in the art employ binary encoding with the electrophoric tags attached to amine groups, attaching these tags directly to the bead matrix provides far greater versatility in the structures that can be prepared in encoded combinatorial libraries. Attached in this way, the tags and their linker are nearly as unreactive as the bead matrix itself. Two binary-encoded combinatorial libraries have been reported where the electrophoric tags are attached directly to the solid phase (Ohlmeyer et al. (1995) *PNAS* 92:6027–6031) and provide guidance for generating the subject compound library. Both libraries were constructed using an orthogonal attachment strategy in which the library member was linked to the solid support by a photolabile linker and the tags were attached through a linker cleavable only by vigorous oxidation. Because the library members can be repetitively partially photoeluted from the solid support, library members can be utilized in multiple assays. Successive photoelution also permits a very high throughput iterative screening strategy: first, multiple beads are placed in 96-well microtiter plates; second, compounds are partially detached and transferred to assay plates; third, a metal binding assay identifies the active wells; fourth, the corresponding beads are rearrayed singly into new microtiter plates; fifth, single active compounds are identified; and sixth, the structures are decoded.

EXEMPLIFICATION

The invention now being generally described, it will be more readily understood by reference to the following examples which are included merely for purposes of illustration of certain aspects and embodiments of the present invention, and are not intended to limit the invention.

EXAMPLE 1

Commercially available benzophenone imine serves as a convenient ammonia equivalent in the palladium-catalyzed amination of aryl halides and triflates. The benzophenone imine adducts can be cleaved directly to the corresponding primary anilines by catalytic hydrogenation or treatment with hydroxylamine hydrochloride or a catalytic amount of HCl in wet THF.

A number of useful protocols for the palladium- and nickel-catalyzed conversion of aryl bromides,[1a,b] chlorides,[1c] iodides[1d] and triflates[1e,f] to the corresponding aniline derivatives have been recently reported. While these procedures are effective for the preparation of substituted anilines, no simple means for the preparation of the unsubstituted primary anilines has been described. We now have found that commercially available benzophenone imine serves as a convenient surrogate for ammonia in these coupling procedures (Eq 1). The benzophenone imines formed can be isolated in pure form or can be converted under a variety of conditions to the corresponding anilines in a straightforward manner.[2]

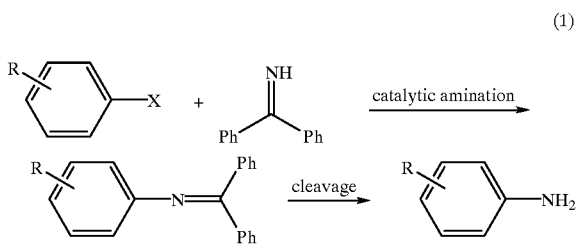

(1)

During the course of our work on the synthesis of oligoaniline derivatives for study as conducting and sensor materials we had reason to employ a protecting group for a primary aniline. We found that benzophenone imines served this role in a convenient manner; they were easily formed,[3] stable to base and mild acid, and cleaved under a variety of conditions. It occurred to us that the protected anilines might be directly accessible using our previously reported methods for the amination of aryl halides and triflates.

In general, we found that the coupling reactions with benzophenone imine were efficient. Shown in Table 1, are four examples of substrates which were converted to benzophenone imines.[4] The diphenyl ketimine moiety instilled or enhanced crystallinity in the products which allowed for facile purification by recrystallization from MeOH. Subsequent cleavage to the primary aniline was effected by acidic hydrolysis, hydrogenolysis, or

TABLE 1

Palladium-Catalyzed Amination of Aryl Bromides and Triflates

| Entry | Substrate | Product | Yield (%) |
|---|---|---|---|
| 1 | (1-naphthyl OTf) | (1-naphthyl N=CPh₂) | 85%[a, ref. 5] |

TABLE 1-continued

Palladium-Catalyzed Amination of Aryl Bromides and Triflates

[Reaction scheme: R-substituted aryl-X + HN=CPh₂ → (catalytic amination) → R-substituted aryl-N=CPh₂ → (cleavage) → R-substituted aryl-NH₂]

| Entry | Aryl halide | Imine product | Yield |
|---|---|---|---|
| 2 | 4-tBu-C₆H₄-Br | 4-tBu-C₆H₄-N=CPh₂ | 90%[b] |
| 3 | 4-MeO₂C-C₆H₄-Br | 4-MeO₂C-C₆H₄-N=CPh₂ | 75%[c] |
| 4 | BOC-N(4-Br-C₆H₄)₂ | BOC-N(4-(Ph₂C=N)-C₆H₄)₂ | 91%[d] |

| Entry | Cleavage Conditions | Product | Yield (%)[e] |
|---|---|---|---|
| 1 | cat. HCl, wet THF, rt | 1-naphthylamine (NH₂) | 98% |
| 2 | NH₄⁺HCO₂⁻, cat Pd/C, MeOH/60° C. | 4-tBu-C₆H₄-NH₂ | 84% |
| 3 | NH₂OH·HCl, NaOAc, MeOH/rt | 4-MeO₂C-C₆H₄-NH₂ | 88% |
| 4 | NH₄⁺HCO₂⁻, cat Pd/C, MeOH/60° C. | BOC-N(4-H₂N-C₆H₄)₂ | 95% |

[a] 1 mol % Pd(OAc)₂, 1.5 mol % BINAP, 1.4 eq Cs₂CO₃, THF, 65° C., 16 h.
[b] 0.25 mol % Pd₂(dba)₃, 0.75 mol % BINAP, 1.4 eq NaOtBu, toluene, 80° C., 13 h.
[c] 2 mol % Pd(OAc)₂, 3 mol % BINAP, 1.4 eq Cs₂CO₃, toluene, 100° C., 5 h.
[d] 0.25 mol % Pd₂(dba)₃, 0.75 mol % BINAP, 1.4 eq NaOtBu, toluene, 80° C., 6 h.
[e] Isolated yields reported are an average of two runs.

transamination with hydroxylamine.[6] In many cases it may be advantageous to retain the imine moiety after coupling for use as a protecting group of the primary aniline because of its robust nature[7] and facile removal.[2]

Catalytic amination was carried out on additional substrates using benzophenone imine as shown in Table 2. The yields reported correspond to isolation of the primary aniline for the two step sequence of amination and imine cleavage. The methodology is effective with aryl chlorides, bromides, iodides and triflates. Couplings involving aryl triflates employed $Cs_2CO_3$ in place of NaOtBu to avoid hydrolysis of the triflate.[1e,g] Benzophenone imine serves as an ideal coupling partner since it is relatively unhindered, the nitrogen is $sp^2$ hybridized,[8] and can not undergo palladium-catalyzed β-hydride elimination. Due to the variety of methods available for imine cleavage, conditions were found for selective diphenyl ketimine removal in products containing a benzylic acetal (entry 4), a methyl ester (entries 8 and 10), or a benzylic ketone (entry 9).

In summary, we have demonstrated the utility of employing benzophenone imine as a substitute for ammonia in the palladium-catalyzed amination of aryl halides and triflates. The couplings and subsequent deprotections proceed in uniformly high yields. When it is desirable to retain the imine as a means of masking the primary amine, the diphenyl ketimine adducts may be isolated as crystalline solids or purified by chromatography on silica gel in high yield.

TABLE 2

Palladium-Catalyzed Amination and Subsequent Imine Cleavage

| Entry | Substrate | Product | Time | Cleavage[ref. 6] | Yield (%)[e] |
|---|---|---|---|---|---|
| 1 | 2-bromoanisole | 2-methoxyaniline | 5 h[a] | B | 87 |
| 2 | 2-bromo-1,4-dimethylbenzene | 2,5-dimethylaniline | 19 h[a] | B | 77 |
| 3 | 4-bromobenzonitrile | 4-aminobenzonitrile | 1.5 h[a] | A | 97 |
| 4 | 3-bromophenyl-1,3-dioxolane | 3-aminophenyl-1,3-dioxolane | 1.5 h[a] | A | 89 |
| 5 | 1-bromo-4-iodobenzene | 4-bromoaniline | 48 h[b] | C | 91 |
| 6 | 4-iodoanisole | 4-methoxyaniline | 14 h[b] | A | 88 |
| 7 | 4-cyanophenyl triflate | 4-aminobenzonitrile | 4.5 h[c] | A | 84 |
| 8 | methyl 3-(trifluoromethylsulfonyloxy)benzoate | methyl 3-aminobenzoate | 20 h[c] | A | 80 |

TABLE 2-continued

Palladium-Catalyzed Amination and Subsequent Imine Cleavage

| Entry | Substrate | Product | Time | Cleavage[ref. 6] | Yield (%)[e] |
|---|---|---|---|---|---|
| 9 | 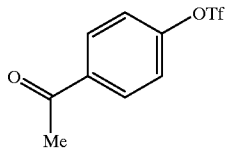 | 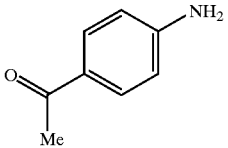 | 4 h[c] | C | 83 |
| 10 | 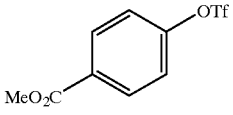 | 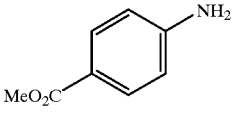 | 5 h[c] | A | 89 |
| 11 | 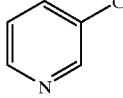 | 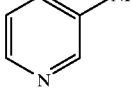 | 16 h[d] | A | 81 |

[a] 0.25 mol % $Pd_2(dba)_3$, 0.75 mol % BINAP, 1.4 eq NaOtBu, toluene, 80° C.
[b] 1.0 mol % $Pd_2(dba)_3$, 3.0 mol % BINAP, 1.4 eq NaOtBu, 1.4 eq 18-Crown-6, THF, rt.
[c] 3 mol % $Pd(OAc)_2$, 4.5 mol % BINAP, 1.4 eq $Cs_2CO_3$, THF, 65° C.
[d] 5 mol % $Ni(COD)_2$, 10 mol % DPPF, 1.4 eq NaOtBu, toluene, 100° C.[ref. 1f]
[e] Isolated yields reported are an average of two runs. All compounds were characterized by NMR ($^1$H, $^{13}$C), and IR. All aniline products are commercially available except for entry 4 in Table 1 and entry 4 in Table 2.[ref. 9] Combustion analyses were obtained for all imine and aniline products which were not commercially available.

REFERENCES AND ENDNOTES FOR EXAMPLE 1

(1) (a) Wolfe, J. P.; Wagaw, S.; Buchwald, S. L. *J. Am. Chem. Soc.* 1996, 118, 7215. (b) Driver, M. S.; Hartwig, J. F. *J. Am. Chem. Soc.* 1996, 118, 7217. (c) Wolfe, J. P.; Buchwald, S. L. *J. Am. Chem. Soc.*, in press. (d) Wolfe, J. P.; Buchwald, S. L. Manuscript submitted. (e) Wolfe, J. P.; Buchwald, S. L. *J. Org. Chem.* 1997, 62, 1264 and references cited therein. (f) Louie, J.; Driver, M. S.; Hamann, B.C.; Hartwig, J. F. *J. Org. Chem.* 1997, 62, 1268 and references cited therein. (g) Ahman, J.; Buchwald, S. L. *Tetrahedron Lett.* 1997, accompanying paper in this issue.

(2) (a) Wessjohann, L.; McGaffin, G.; de Meijere, A. *Synthesis,* 1989, 359. (b) Fasth, K.-J.; Antoni, G.; Långström, B. *J. Chem. Soc., Perkin Trans. 1* 1988, 3081. (c) O'Donnell, M. J.; Boniece, J. M.; Earp, S. E. *Tetrahedron Lett.* 1978, 2641.

(3) Taguchi, K.; Westheimer, F. H. *J. Org. Chem.* 1971, 36, 1570.

(4) Representative Procedure: An oven-dried Schlenk tube was charged with $Pd_2(dba)_3$ (0.00125 mmol) and BINAP (0.00375 mmol), and purged with argon. To the flask was added 4-t-butylbromobenzene (1.00 mmol), benzophenone imine (1.20 mmol), NaOtBu (1.40 mmol) and toluene (4 mL), and the mixture was heated to 80° C. with stirring until the starting material had been consumed as judged by GC analysis. The mixture was cooled to room temperature, diluted with ether (10×volume of toluene), filtered, and concentrated. The crude product was then recrystallized from MeOH. Yellow crystals of the diphenyl ketimine adduct were isolated in 90% yield.

(5) The imine product has been previously prepared: Seno, M.; Shirashi, S.; Suzuki, Y.; Asahara, T. *Bull. Chem. Soc. Jpn.* 1978, 51, 1413. It was found that DBU could be used in place of $Cs_2CO_3$ to carry out the Pd-catalyzed (3 mol %) coupling of α-naphthyltriflate and benzophenone imine in 82% yield at 110° C. in toluene (24 h). Utilizing DBU as a base has not been found to be general in scope.

(6) General Procedures for Imine Cleavage:

Method A (Transamination with Hydroxylamine) To a solution of the imine adduct in MeOH (0.1 M) at rt was added NaOAc (2.4 eq) and hydroxylamine hydrochloride (1.8 eq). Oxime formation was usually complete in 15 to 30 minutes. The solution was then partitioned between 0.1 M NaOH and $CH_2Cl_2$. The organic layer was dried over anhydrous $Na_2SO_4$ and concentrated in vacuo. The product was purified by chromatography on silica gel.

Method B (Hydrogenolysis) A solution of the imine adduct, ammonium formate (15 eq) and 5% Pd/C (10 mol %) was heated to 60° C. in MeOH (0.2 M in imine). After 2 h reduction was usually complete. The solution was cooled to rt and diluted with $CH_2Cl_2$ (5×volume MeOH) to be passed through a plug of celite. The organic solution was washed with 0.1 M NaOH, dried over anhydrous $Na_2SO_4$ and concentrated in vacuo. The product was purified by chromatography on silica gel.

Method C (Acidic Hydrolysis) To a solution of the imine adduct in THF (0.3 M) was added aqueous 2.0 M HCl (added 5% by volume of THF). After 5–20 minutes hydrolysis was complete and the reaction mixture was partitioned between 0.5 M HCl and 2:1 hexane/EtOAc. The aqueous layer was separated and made alkaline. The product aniline was extracted with $CH_2Cl_2$, dried over anhydrous $Na_2SO_4$ and concentrated in vacuo.

(7) The imine adducts are stable to purification by chromatography on silica gel. As a further demonstration of the stability of the diphenyl ketimine, we have found that it was possible to carry out halogen metal exchange (n-BuLi, THF, −78° C.) on the benzophenone imine protected 4-bromoaniline without substantial (<5%) addition to the imine.
(8) Reductive elimination from palladium should be more facile (electronically) for an imine than an amine.
(9) Manecke, G.; Vogt, H. G. *J. Solid-Phase Biochem.* 1979, 4, 233.

EXAMPLE 2
Synthesis of 2-Amino-2'-(4'-methoxybenzyloxy)-1,1'-binaphthyl

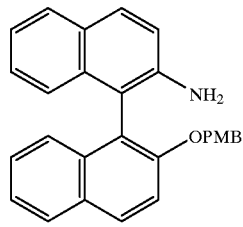

A flask containing 2-(trifluoromethanesulfonyloxy)-2'-(4'-methoxybenzyloxy)-1,1'-binaphthyl (539 mg, 1.00 mmol), benzophenone imine (503 µL, 3.00 mmol), palladium acetate (11.2 mg, 0.0500 mmol), bis[2-(diphenylphosphino)phenyl]ether [DPE-phos] (40.4 mg, 0.0750 mmol), and triethylamine (70 µL) was purged with a gentle stream of argon for 20 minutes while stirring the mixture at room temperature. After this time, cesium carbonate (488 mg, 1.50 mmol) was added under a heavy stream of argon. The reaction mixture was then heated to 90° C. under an argon atmosphere for 32 hours. The reaction mixture was then cooled to room temperature and diluted with 30 mL of ethyl acetate. The organic solution was washed with a saturated aqueous sodium chloride solution (30 mL). The organic solution was dried over anhydrous sodium sulfate and concentrated in vacuo. The residue was redissolved in 10 mL of tetrahydrofuran and 10 mL of ethanol to be treated with 2.0 mL of 2.0 M aqueous hydrochloric acid. The solution was stirred for 1 hour and then was diluted with 30 mL of aqueous 2.0 M sodium hydroxide. The organics were extracted with 40 mL of ethyl acetate. The organic layer was washed with 30 mL of a saturated aqueous sodium chloride solution. The organic solution was dried over anhydrous sodium sulfate and was concentrated in vacuo. The product was isolated as a white solid (369 mg, 91%) by crystallization from isopropanol.

EXAMPLE 3
Synthesis of (N-Diphenylmethylene)-4-tert-butylaniline

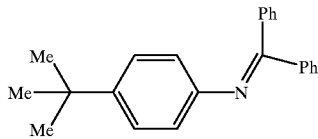

Palladium acetate (2.3 mg, 10 µmol) and bis(2-(diphenylphosphino)phenyl)ether [DPEphos] (8.1 mg, 15 µmol) were placed in an oven-dried test tube, which was capped with a rubber septum and purged for 3 min with argon. Benzophenone imine (0.180 mL, 1.07 mmol) was added via syringe, followed by 1-bromo-4-tert-butyl benzene (0.173 mL, 1.00 mmol), and toluene (4 mL). The resulting mixture was stirred for several minutes, affording a clear yellow solution. The tube was opened and solid sodium tert-butoxide (0.135 g, 1.40 mmol) was added in one portion, causing the yellow color to deepen. The tube was again capped with the septum and purged for 5 min with argon. The reaction mixture was heated to 80° C. with stirring. A white precipitate formed within a few minutes. After 40 minutes, gas chromatographic analysis showed complete consumption of aryl bromide. The reaction mixture was cooled to room temperature and taken up in diethyl ether (50 mL). The resulting mixture was washed with saturated aqueous sodium chloride (25 mL), dried over potassium carbonate, filtered, and concentrated in vacuo. Recrystallization of the residual solid from methanol afforded the title compound as yellow crystals (0.283 g, 90%).

EXAMPLE 4
Synthesis of (N-Diphenylmethylene)-4-tert-butylaniline

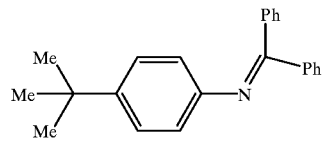

Tris(dibenzylideneacetone)dipalladium (4.6 mg, 5 µmol), bis(2-(diphenylphosphino)phenyl)ether [DPE-phos] (8.1 mg, 15 µmol) and sodium tert-butoxide (0.135 g, 1.40 mmol) were placed in an oven-dried test tube, which was capped with a rubber septum and purged for 5 min with argon. Benzophenone imine (0.180 mL, 1.07 mmol) was added via syringe, followed by 1-bromo-4-tert-butyl benzene (0.173 mL, 1.00 mmol), and toluene (4 mL). The resulting mixture was heated to 80° C. with stirring, affording a clear red solution. A white precipitate was visible after 30 min. Analysis of the reaction mixture by gas chromatography after 3 h 40 min indicated complete consumption of aryl bromide. The reaction mixture was cooled to room temperature and taken up in diethyl ether (50 mL). The resulting mixture was washed with saturated aqueous sodium chloride solution (25 mL), dried over potassium carbonate, filtered, and concentrated in vacuo. Purification of the residual solid by flash chromatography on silica gel, using 9:1 hexanes/ethyl acetate as the eluent, afforded the product as yellow crystals (0.299 g, 95%)

EXAMPLE 5
Synthesis of N-(Diphenylmethylene)-3-methoxyaniline

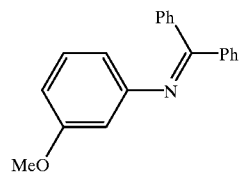

An oven-dried test tube was charged with tris (dibenzylideneacetone) dipalladium (4.6 mg, 0.005 mmol) and bis(2-(diphenylphosphino)phenyl)ether [DPE-phos] (8.2 mg, 0.015 mmol), capped with a rubber septum, evacuated and refilled with argon. Benzophenone imine (190 mg, 1.05 mmol), 3-bromoanisole (187 mg, 1.0 mmol) and toluene (2 mL) were added via syringe. The resulting solution was stirred at rt for 5 minutes. The tube was opened and sodium tert-butoxide (135 mg, 1.4 mmol) was added. The tube was again capped with the septum, and additional

EXAMPLE 6
Synthesis of N-(Diphenylmethylene)-4-methoxyaniline

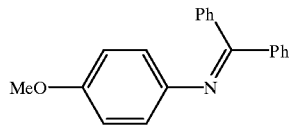

An oven-dried test tube was charged with tris(dibenzylideneacetone)dipalladium (4.6 mg, 0.005 mmol) and bis(2-(diphenylphosphino)phenyl)ether [DPE-phos] (8.2 mg, 0.015 mmol), capped with a rubber septum, evacuated and refilled with argon. Benzophenone imine (190 mg, 1.05 mmol), 4-bromoanisole (187 mg, 1.0 mmol) and toluene (2 mL) were added via syringe. The resulting solution was stirred at rt for 5 minutes. The tube was opened and sodium tert-butoxide (135 mg, 1.4 mmol) was added. The tube was again capped with the septum, and additional toluene (2 mL) was added via syringe to wash the solid from the test tube wall into the solution. The solution was stirred at room temperature with a gentle argon purge for 5 minutes, then heated at 80° C. for 4 hours and 30 minutes. The reaction mixture was cooled to room temperature, washed with saturated aqueous sodium chloride (2 mL), and the organic layer was concentrated in vacuo. The product was isolated as a yellow oil (238 mg, 83%) by flash chromatography on silica gel using 5% ethyl acetate in hexanes as eluent.

EXAMPLE 7
Synthesis of N-(Diphenylmethylene)-2-methoxyaniline

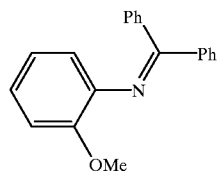

An oven-dried test tube was charged with tris(dibenzylideneacetone)dipalladium (4.6 mg, 0.005 mmol) and bis(2-(diphenylphosphino)phenyl)ether [DPE-phos] (8.2 mg, 0.015 mmol), capped with a rubber septum, evacuated and refilled with argon. Benzophenone imine (190 mg, 1.05 mmol), 2-bromoanisole (187 mg, 1.0 mmol) and toluene (2 mL) were added via syringe. The resulting solution was stirred at rt for 5 minutes. The tube was opened and sodium tert-butoxide (135 mg, 1.4 mmol) was added. The tube was again capped with the septum, and additional toluene (2 mL) was added via syringe to wash the solid from the test tube wall into the solution. The solution was stirred at room temperature with a gentle argon purge for 23 minutes, then heated at 80° C. for 2 hours and 10 minutes. The reaction mixture was cooled to room temperature and 1 mL ether was added. This solution was washed with saturated aqueous sodium chloride (2 mL) and the organic layer was concentrated in vacuo. The product was isolated as a yellow oil (216 mg, 75%) by flash chromatography on silica gel using 10% ethyl acetate in hexanes as eluent.

EXAMPLE 8
Synthesis of 2-(3-N-(Diphenalmethylene)phenyl)-1,3-dioxolane

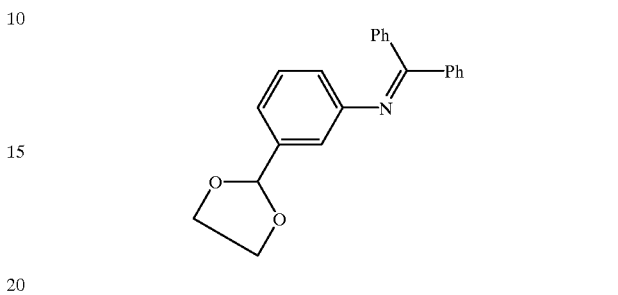

An oven-dried test tube was charged with tris(dibenzylideneacetone)dipalladium (4.6 mg, 0.005 mmol) and bis(2-(diphenylphosphino)phenyl)ether [DPE-phos] (8.2 mg, 0.015 mmol), capped with a rubber septum, evacuated and refilled with argon. Benzophenone imine (190 mg, 1.05 mmol), 2-(3-bromophenyl)1,3-dioxolane (229 mg, 1.0 mmol) and toluene (3 mL) were added via syringe. The resulting solution was stirred at rt for 5 minutes. The tube was opened and sodium tert-butoxide (135 mg, 1.4 mmol) was added. The tube was again capped with the septum, and additional toluene (2 mL) was added via syringe to wash the solid from the test tube wall into the solution. The solution was stirred at room temperature with a gentle argon purge for 5 minutes, then heated at 80° C. for 3 hours and 50 minutes. The reaction mixture was cooled to room temperature, washed with saturated aqueous sodium chloride (2 mL), and the organic layer was filtered through celite and concentrated in vacuo. The product was isolated as an orange solid (257 mg, 78%) by recrystalization from hot methanol.

EXAMPLE 9
Synthesis of N-(Diphenylmethylene)-3-fluoroaniline

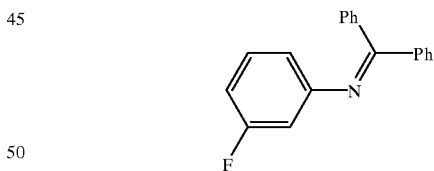

An oven-dried test tube was charged with tris(dibenzylideneacetone)dipalladium (4.6 mg, 0.005 mmol) and bis(2-(diphenylphosphino)phenyl)ether [DPE-phos] (8.2 mg, 0.015 mmol), capped with a rubber septum, evacuated and refilled with argon. Benzophenone imine (190 mg, 1.05 mmol), 3-bromofluorobenzene (175 mg, 1.0 mmol) and toluene (2 mL) were added via syringe. The resulting solution was stirred at rt for 5 minutes. The tube was opened and sodium tert-butoxide (135 mg, 1.4 mmol) was added. The tube was again capped with the septum, and additional toluene (2 mL) was added via syringe to wash the solid from the test tube wall into the solution. The solution was stirred at room temperature with a gentle argon purge for 5 minutes, then heated at 80° C. for 3 hours and 5 minutes. The reaction mixture was cooled to room temperature and washed with saturated aqueous sodium chloride (2 mL). The organic layer was filtered through celite and concentrated in vacuo. The product was isolated as a yellow solid (210 mg, 76%) by recrystalization from hot methanol.

EXAMPLE 10
Synthesis of N-(Diphenylmethylene)-2-chloroaniline

An oven-dried test tube was charged with tris(dibenzylideneacetone)dipalladium (4.6 mg, 0.005 mmol) and bis(2-(diphenylphosphino)phenyl)ether [DPE-phos] (8.2 mg, 0.015 mmol), capped with a rubber septum, evacuated, and refilled with argon. Benzophenone imine (190 mg, 1.05 mmol), 2-bromochlorobenzene (191 mg, 1.0 mmol) and toluene (2 mL) were added via syringe. The resulting solution was stirred at rt for 5 minutes. The tube was opened and sodium tert-butoxide (135 mg, 1.4 mmol) was added. The tube was again capped with the septum, and additional toluene (2 mL) was added via syringe to wash the solid from the test tube wall into the solution. The solution was stirred at room temperature with a gentle argon purge for 5 minutes, then heated at 80° C. for 2 hours and 5 minutes. The reaction mixture was cooled to room temperature and washed with saturated aqueous sodium chloride (2 mL). The organic layer was filtered through celite and concentrated in vacuo. The product was isolated as a yellow solid (208 mg, 71%) by flash chromatography on silica gel using 5% ethyl acetate in hexanes as eluent.

EXAMPLE 11
Synthesis of N-(Diphenylmethylene)-4-chloroaniline

An oven-dried test tube was charged with tris(dibenzylideneacetone)dipalladium (4.6 mg, 0.005 mmol), bis(2-(diphenylphosphino)phenyl)ether [DPE-phos] (8.2 mg, 0.015 mmol) and 4-bromochlorobenzene (191 mg, 1.0 mmol), capped with a rubber septum, evacuated, and refilled with argon. Benzophenone imine (190 mg, 1.05 mmol) and toluene (2 mL) were added via syringe. The resulting solution was stirred at rt for 5 minutes. The tube was opened and sodium tert-butoxide (135 mg, 1.4 mmol) was added. The tube was again capped with the septum, and additional toluene (2 mL) was added via syringe to wash the solid from the test tube wall into the solution. The solution was stirred at room temperature with a gentle argon purge for 5 minutes, then heated at 80° C. for 1 hour and 30 minutes. The reaction mixture was cooled to room temperature, washed with saturated aqueous sodium chloride (2 mL), and the organic layer was concentrated in vacuo. The product was isolated as a yellow solid (221 mg, 76%) by flash chromatography on silica gel using 5% ethyl acetate in hexanes as eluent.

All of the references and publications cited herein are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. The method depicted in Scheme 1:

Scheme 1

$$ArX + RN{=}\begin{array}{c}R_1\\R_2\end{array} \xrightarrow{\text{transition metal catalyst, base, heat}} \begin{array}{c}R_1\\Ar{-}N{=}\\R_2\end{array}$$

wherein:
Ar is selected from the group consisting of optionally substituted monocyclic and polycyclic aromatic and heteroaromatic moieties;
X is selected from the group consisting of Cl, Br, I, $-OS(O)_2$halogen, $-OS(O)_2$alkyl, and $-OS(O)_2$aryl;
the transition metal catalyst comprises a transition metal selected from Groups 5–12 of the periodic table;
R is selected from the group consisting of hydrogen, trialkylstannyl, triarylstannyl, trialkylsilyl, triarylsilyl, lithium, sodium, potassium, magnesium halide, calcium halide, $-B(OH)_2$, and groups that are replaced by hydrogen under the reaction conditions;
$R_1$ and $R_2$, each independently represent hydrogen, or an optionally substituted alkyl, alkenyl, alkynyl, heteroalkyl, aryl, heteroaryl, arylalkyl, or heteroarylalkyl group, or $-(CH_2)_m-R_8$; or $R_1$ and $R_2$ taken together form an optionally substituted ring;
the base is selected from the group consisting of alkoxides, carbonates, amides, phosphates, fluorides;
$R_8$ represents an optionally substituted aryl, cycloalkyl, cycloalkenyl, heterocycle or polycycle; and
m is an integer in the range of 0 to 8 inclusive.

2. The method of claim 1, wherein R is hydrogen.

3. The method of claim 1, wherein $R_1$ and $R_2$ are independently selected from the group consisting of alkyl, aryl, and arylalkyl.

4. The method of claim 1, wherein $R_1$ and $R_2$ taken together form an optionally substituted carbocycle; said carbocycle having between three and eight backbone carbons.

5. The method of claim 1, wherein $R_1$ and $R_2$ both represent phenyl; and R represents hydrogen.

6. The method of claim 1, wherein the method is intramolecular.

7. The method of claim 1, wherein X represents Br, I, OTs, OTf, OMs, or ONf.

8. The method of claim 1, wherein the transition metal catalyst comprises a transition metal selected from Groups 8–10 of the periodic table.

9. The method of claim 1, wherein the transition metal catalyst comprises a transition metal selected from Group 10 of the periodic table.

10. The method of claim 1, wherein the transition metal catalyst comprises palladium.

11. The method of claim 1, wherein the transition metal catalyst is present in less than about 20 mol % relative to ArX.

12. The method of claim 1, wherein the transition metal catalyst is present in less than about 10 mol % relative to ArX.

13. The method of claim 1, wherein the transition metal catalyst is present in less than about 5 mol % relative to ArX.

14. The method of claim 1, wherein the transition metal catalyst is present in less than about 3 mol % relative to ArX.

15. The method of claim 1, wherein the transition metal catalyst is present in less than about 1 mol % relative to ArX.

16. The method of claim 1, wherein the product is produced in greater than about 50% yield relative to ArX.

17. The method of claim 1, wherein the product is produced in greater than about 70% yield relative to ArX.

18. The method of claim 1, wherein the product is produced in greater than about 80% yield relative to ArX.

19. The method of claim 1, wherein the product is produced in greater than about 90% yield relative to ArX.

20. The method of claim 2, wherein X represents Br, I, OTs, OTf, OMs, or ONf.

21. The method of claim 20, wherein the transition metal catalyst comprises a transition metal selected from Groups 8–10 of the periodic table.

22. The method of claim 20, wherein the transition metal catalyst comprises a transition metal selected from Group 10 of the periodic table.

23. The method of claim 20, wherein the transition metal catalyst comprises palladium.

24. The method of claim 5, wherein X represents Br, I, OTs, OTf, OMs, or ONf.

25. The method of claim 24, wherein the transition metal catalyst comprises a transition metal selected from Groups 8–10 of the periodic table.

26. The method of claim 24, wherein the transition metal catalyst comprises a transition metal selected from Group 10 of the periodic table.

27. The method of claim 24, wherein the transition metal catalyst comprises palladium.

28. The method of claim 24, 25, 26, or 27, wherein the transition metal catalyst is present in less than about 20 mol % relative to ArX.

29. The method of claim 24, 25, 26, or 27, wherein the transition metal catalyst is present in less than about 10 mol % relative to ArX.

30. The method of claim 24, 25, 26, or 27, wherein the transition metal catalyst is present in less than about 5 mol % relative to ArX.

31. The method of claim 24, 25, 26, or 27, wherein the transition metal catalyst is present in less than about 3 mol % relative to ArX.

32. The method of claim 24, 25, 26, or 27, wherein the transition metal catalyst is present in less than about 1 mol % relative to ArX.

33. The method of claim 24, 25, 26, or 27, wherein the product is produced in greater than about 50% yield relative to ArX.

34. The method of claim 24, 25, 26, or 27, wherein the product is produced in greater than about 70% yield relative to ArX.

35. The method of claim 24, 25, 26, or 27, wherein the product is produced in greater than about 80% yield relative to ArX.

36. The method of claim 24, 25, 26, or 27, wherein the product is produced in greater than about 90% yield relative to ArX.

37. The method of claim 24, 25, 26, or 27, wherein the transition metal catalyst is present in less than about 10 mol % relative to ArX; and the product is produced in greater than about 70% yield relative to ArX.

38. The method of claim 24, 25, 26, or 27, wherein the transition metal catalyst is present in less than about 5 mol % relative to ArX; the product is produced in greater than about 70% yield relative to ArX.

39. The method of claim 24, 25, 26, or 27, wherein the transition metal catalyst is present in less than about 3 mol % relative to ArX; and the product is produced in greater than about 70% yield relative to ArX.

40. The method of claim 24, 25, 26, or 27, wherein the transition metal catalyst is present in less than about 1 mol % relative to ArX; and the product is produced in greater than about 70% yield relative to ArX.

41. The method of claim 1, 2, 3, 4, 5, 6, 7, 8, 9, 10, 24, 25, 26, or 27, further comprising the step of hydrolyzing the imine moiety of the N-aryl imine product to provide a primary arylamine.

42. The method of claim 1, 2, 3, 4, 5, 6, 7, 8, 9, 10, 24, 25, 26, or 27, further comprising the step of treating the N-aryl imine product with a primary amine to provide a primary arylamine.

43. The method of claim 1, 2, 3, 4, 5, 6, 7, 8, 9, 10, 24, 25, 26, or 27, further comprising the step of hydrogenating the N-aryl imine product to provide a primary arylamine.

44. The method depicted in Scheme 3:

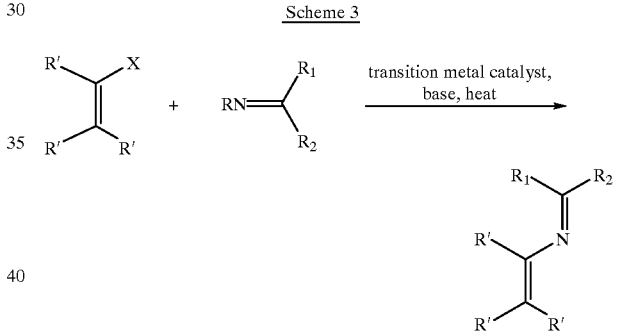

Scheme 3 wherein:
X is selected from the group consisting of Cl, Br, I, —OS(O)$_2$halogen, —OS(O)$_2$alkyl, and —OS(O)$_2$aryl;
the transition metal catalyst comprises a transition metal selected from Groups 5–12 of the periodic table;
R is selected from the group consisting of hydrogen, trialkylstannyl, triarylstannyl, trialkylsilyl, triarylsilyl, lithium, sodium, potassium, magnesium halide, calcium halide, —B(OH)$_2$, and groups that are replaced by hydrogen under the reaction conditions;
R$_1$ and R$_2$, each independently represent hydrogen, or an optionally substituted alkyl, alkenyl, alkynyl, heteroalkyl, aryl, heteroaryl, arylalkyl, or heteroarylalkyl group, or —(CH$_2$)$_m$—R$_8$; or R$_1$ and R$_2$ taken together form an optionally substituted ring;
R' is selected, independently for each occurrence, and as valence and stability permit, from the group consisting of hydrogen, halogen, alkyl, alkenyl, alkynyl, heteroalkyl, aryl, heteroaryl, arylalkyl, heteroarylalkyl, formyl, acyl, amino, acylamino, amido, amidino, cyano, nitro, sulfonyl, sulfoxido, sulfate, sulfonate, sulfamoyl, sulfonamido, phosphoryl, phosphonate, phosphinate, —(CH$_2$)$_m$—R$_8$, —(CH$_2$)$_m$—OH, —(CH$_2$)$_m$—O-alkyl, —(CH$_2$)$_m$—O-alkenyl, —(CH$_2$)$_m$—O-aryl, —(CH$_2$)$_m$—O—(CH$_2$)$_m$—R$_8$, —(CH$_2$)$_m$—SH, —(CH$_2$)$_m$—S-alkyl, —(CH$_2$)$_m$—S-alkenyl, —(CH$_2$)$_m$—S-aryl, —(CH$_2$)$_m$—S—(CH$_2$)$_m$—R$_8$, a solid support, and a polymeric support;

the base is selected from the group consisting of alkoxides, carbonates, amides, phosphates, and fluorides;

R$_8$ represents an optionally substituted aryl, cycloalkyl, cycloalkenyl, heterocycle or polycycle; and m, independently for each occurrence, is an integer in the range of 0 to 8 inclusive.

45. The method of claim 44, wherein R is hydrogen.

46. The method of claim 44, wherein R$_1$ and R$_2$ are independently selected from the group consisting of alkyl, aryl, and arylalkyl groups.

47. The method of claim 44, wherein R$_1$ and R$_2$ taken together form an optionally substituted carbocycle; said carbocycle having between three and eight backbone carbons.

48. The method of claim 44, wherein R$_1$ and R$_2$ both represent phenyl; and R represents hydrogen.

49. The method of claim 44, wherein the method is intramolecular.

50. The method of claim 44, wherein X represents Br, I, OTs, OTf, OMs, or ONf.

51. The method of claim 44, wherein the transition metal catalyst comprises a transition metal selected from Groups 8–10 of the periodic table.

52. The method of claim 44, wherein the transition metal catalyst comprises a transition metal selected from Group 10 of the periodic table.

53. The method of claim 44, wherein the transition metal catalyst comprises palladium.

54. The method of claim 44, wherein the transition metal catalyst is present in less than about 20 mol % relative to (R')(X)CC(R')$_2$.

55. The method of claim 44, wherein the transition metal catalyst is present in less than about 10 mol % relative to (R')(X)CC(R')$_2$.

56. The method of claim 44, wherein the transition metal catalyst is present in less than about 5 mol % relative to (R')(X)CC(R')$_2$.

57. The method of claim 44, wherein the transition metal catalyst is present in less than about 3 mol % relative to (R')(X)CC(R')$_2$.

58. The method of claim 44, wherein the transition metal catalyst is present in less than about 1 mol % relative to (R')(X)CC(R')$_2$.

59. The method of claim 44, wherein the product is produced in greater than about 50% yield relative to (R')(X)CC(R')$_2$.

60. The method of claim 44, wherein the product is produced in greater than about 70% yield relative to (R')(X)CC(R')$_2$.

61. The method of claim 44, wherein the product is produced in greater than about 80% yield relative to (R')(X)CC(R')$_2$.

62. The method of claim 44, wherein the product is produced in greater than about 90% yield relative to (R')(X)CC(R')$_2$.

63. The method of claim 45, wherein X represents Br, I, OTs, OTf, OMs, or ONf.

64. The method of claim 63, wherein the transition metal catalyst comprises a transition metal selected from Groups 8–10 of the periodic table.

65. The method of claim 63, wherein the transition metal catalyst comprises a transition metal selected from Group 10 of the periodic table.

66. The method of claim 63, wherein the transition metal catalyst comprises palladium.

67. The method of claim 48, wherein X represents Br, I, OTs, OTf, OMs, or ONf.

68. The method of claim 67, wherein the transition metal catalyst comprises a transition metal selected from Groups 8–10 of the periodic table.

69. The method of claim 67, wherein the transition metal catalyst comprises a transition metal selected from Group 10 of the periodic table.

70. The method of claim 67, wherein the transition metal catalyst comprises palladium.

71. The method of claim 67, 68, 69, or 70, wherein the transition metal catalyst is present in less than about 20 mol % relative to (R')(X)CC(R')$_2$.

72. The method of claim 67, 68, 69, or 70, wherein the transition metal catalyst is present in less than about 10 mol % relative to (R')(X)CC(R')$_2$.

73. The method of claim 67, 68, 69, or 70, wherein the transition metal catalyst is present in less than about 5 mol % relative to (R')(X)CC(R')$_2$.

74. The method of claim 67, 68, 69, or 70, wherein the transition metal catalyst is present in less than about 3 mol % relative to (R')(X)CC(R')$_2$.

75. The method of claim 67, 68, 69, or 70, wherein the transition metal catalyst is present in less than about 1 mol % relative to (R')(X)CC(R')$_2$.

76. The method of claim 67, 68, 69, or 70, wherein the product is produced in greater than about 50% yield relative to (R')(X)CC(R')$_2$.

77. The method of claim 67, 68, 69, or 70, wherein the product is produced in greater than about 70% yield relative to (R')(X)CC(R')$_2$.

78. The method of claim 67, 68, 69, or 70, wherein the product is produced in greater than about 80% yield relative to (R')(X)CC(R')$_2$.

79. The method of claim 67, 68, 69, or 70, wherein the product is produced in greater than about 90% yield relative to (R')(X)CC(R')$_2$.

80. The method of claim 67, 68, 69, or 70, wherein the transition metal catalyst is present in less than about 10 mol % relative to (R')(X)CC(R')$_2$; and the product is produced in greater than about 70% yield relative to (R')(X)CC(R')$_2$.

81. The method of claim 67, 68, 69, or 70, wherein the transition metal catalyst is present in less than about 5 mol % relative to (R')(X)CC(R')$_2$; the product is produced in greater than about 70% yield relative to (R')(X)CC(R')$_2$.

82. The method of claim 67, 68, 69, or 70, wherein the transition metal catalyst is present in less than about 3 mol % relative to (R')(X)CC(R')$_2$; and the product is produced in greater than about 70% yield relative to (R')(X)CC(R')$_2$.

83. The method of claim 67, 68, 69, or 70, wherein the transition metal catalyst is present in less than about 1 mol % relative to (R')(X)CC(R')$_2$; and the product is produced in greater than about 70% yield relative to (R')(X)CC(R')$_2$.

84. The method of claim 1, 20, 24, 44, 63, or 67, wherein the transition metal catalyst comprises nickel.

85. The method of claim 1, 2, 5, 7, 10, 20, 24, 27, 44, 45, 48, 50, 53, 63, 67, or 70, wherein the base is selected from the group consisting of alkoxides and carbonates.

86. The method of claim 85, wherein the base is sodium tert-butoxide or cesium carbonate.

87. The method of claim 85, wherein the base is selected from the group consisting of alkoxides and carbonates.

88. The method of claim 84, wherein the base is sodium tert-butoxide or cesium carbonate.

* * * * *

UNITED STATES PATENT AND TRADEMARK OFFICE
CERTIFICATE OF CORRECTION

PATENT NO. : 6,323,366 B1  
APPLICATION NO. : 09/122324  
DATED : November 27, 2001  
INVENTOR(S) : Stephen L. Buchwald et al.

Page 1 of 1

It is certified that error appears in the above-identified patent and that said Letters Patent is hereby corrected as shown below:

In column 1, lines 9-12, replace:

"This invention was supported in part with funds provided by the National Science Foundation and the Office of Naval Research. The government has certain rights in the invention."

with

--This invention was made with government support under grant number N00014-97-1-0197 awarded by the Navy and grant number CHE9421982 awarded by the National Science Foundation. The government has certain rights in this invention.--

Signed and Sealed this
Twenty-eighth Day of June, 2011

David J. Kappos
*Director of the United States Patent and Trademark Office*